(12) United States Patent
Iwashita et al.

(10) Patent No.: US 11,422,098 B2
(45) Date of Patent: Aug. 23, 2022

(54) RADIATION IMAGING SYSTEM, IMAGING CONTROL APPARATUS, AND METHOD

(71) Applicant: CANON KABUSHIKI KAISHA, Tokyo (JP)

(72) Inventors: Atsushi Iwashita, Tokyo (JP); Akira Tsukuda, Kawasaki (JP); Kosuke Terui, Yokohama (JP); Sota Torii, Kawasaki (JP); Takeshi Noda, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 157 days.

(21) Appl. No.: 17/019,638

(22) Filed: Sep. 14, 2020

(65) Prior Publication Data

US 2020/0408704 A1 Dec. 31, 2020

Related U.S. Application Data

(63) Continuation of application No. PCT/JP2019/003593, filed on Feb. 1, 2019.

(30) Foreign Application Priority Data

Mar. 20, 2018 (JP) .............................. JP2018-052916

(51) Int. Cl.
*G01N 23/04* (2018.01)
*G01T 1/17* (2006.01)
*H04N 5/32* (2006.01)

(52) U.S. Cl.
CPC ............... *G01N 23/04* (2013.01); *G01T 1/17* (2013.01); *H04N 5/32* (2013.01)

(58) Field of Classification Search
CPC ........ G01N 23/04; G01N 23/087; G01T 1/17; H04N 5/32; H04N 5/3205; A61B 6/42;
(Continued)

(56) References Cited

U.S. PATENT DOCUMENTS 4,482,918 A 11/1984 Keyes et al.
4,551,800 A * 11/1985 Riederer .................. G06T 5/50
600/407

(Continued)

FOREIGN PATENT DOCUMENTS

CN 106562797 A * 4/2017 .......... A61B 6/4411
EP 3769687 A1 1/2021
(Continued)

OTHER PUBLICATIONS

Han et al., Single-shot dual-energy x-ray imaging with a flat-panel sandwich detector for preclinical imaging, Oct. 17, 2014, Current Applied Physics, vol. 14, pp. 1734-1742. (Year: 2014).*

(Continued)

*Primary Examiner* — Christine S. Kim
(74) *Attorney, Agent, or Firm* — Carter, DeLuca & Farrell LLP

(57) ABSTRACT

An imaging control apparatus obtains a plurality of images at different radiation energies, the images having been obtained as a result of irradiating a subject with radiation whose energy changes during one shot, and detecting, a plurality of times, the radiation that has passed through the subject during the one shot; generates an energy subtraction image by performing energy subtraction processing using a plurality of images; and generates a difference image using a plurality of generated energy subtraction images.

22 Claims, 14 Drawing Sheets

(58) Field of Classification Search
CPC ..... A61B 6/4208; A61B 6/405; A61B 6/4241; A61B 6/481; A61B 6/482; A61B 6/504; A61B 6/4233; A61B 6/5211; A61B 6/54
See application file for complete search history.

(56) References Cited

U.S. PATENT DOCUMENTS

| | | |
|---|---|---|
| 9,035,265 B2 | 5/2015 | Yagi et al. |
| 9,239,390 B2 | 1/2016 | Sato et al. |
| 9,360,562 B2 | 6/2016 | Sato et al. |
| 9,417,333 B2 | 8/2016 | Sato et al. |
| 9,910,169 B2 | 3/2018 | Iwashita et al. |
| 2005/0012046 A1 | 1/2005 | Groh et al. |
| 2006/0109951 A1 | 5/2006 | Popescu |
| 2008/0232549 A1 | 9/2008 | Poorter |
| 2012/0288062 A1 | 11/2012 | Takasaki |
| 2014/0320685 A1 | 10/2014 | Takenaka et al. |
| 2017/0172528 A1 | 6/2017 | Wiedmann et al. |

FOREIGN PATENT DOCUMENTS

| | | |
|---|---|---|
| JP | S58-221580 A | 12/1983 |
| JP | 2002-152593 A | 5/2002 |
| JP | 2011-115562 A | 6/2011 |
| JP | 2011-152280 A | 8/2011 |
| JP | 2018-023671 A | 2/2018 |
| WO | 2007/086369 A | 8/2007 |

OTHER PUBLICATIONS

Supplementary European Search Report issued by the European Patent Office dated Oct. 27, 2021 in corresponding EP Patent Application No. 19770964.5.
International Search Report issued in International Application No. PCT/JP2019/003593 dated Apr. 16, 2019, pp. 1-2.

\* cited by examiner

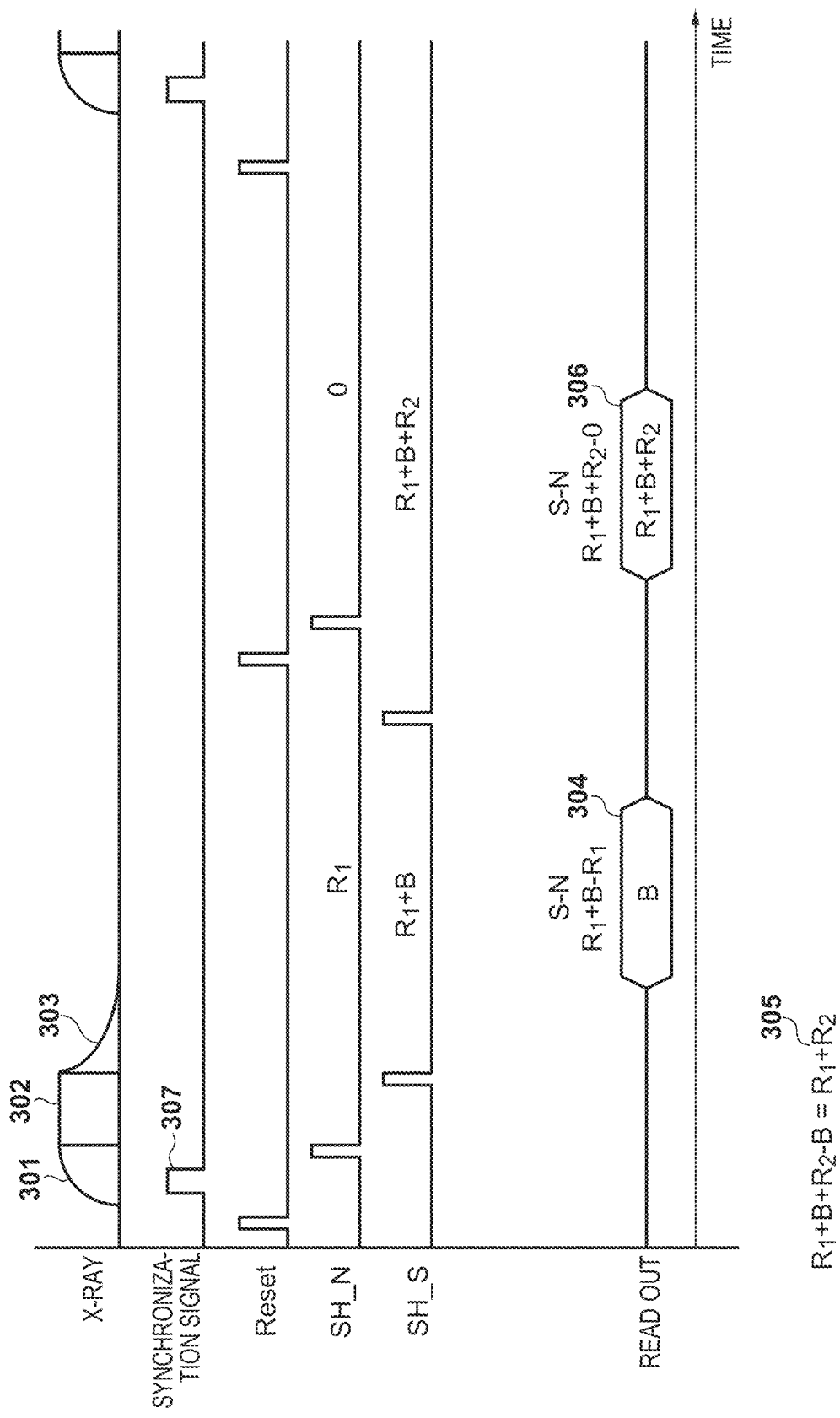

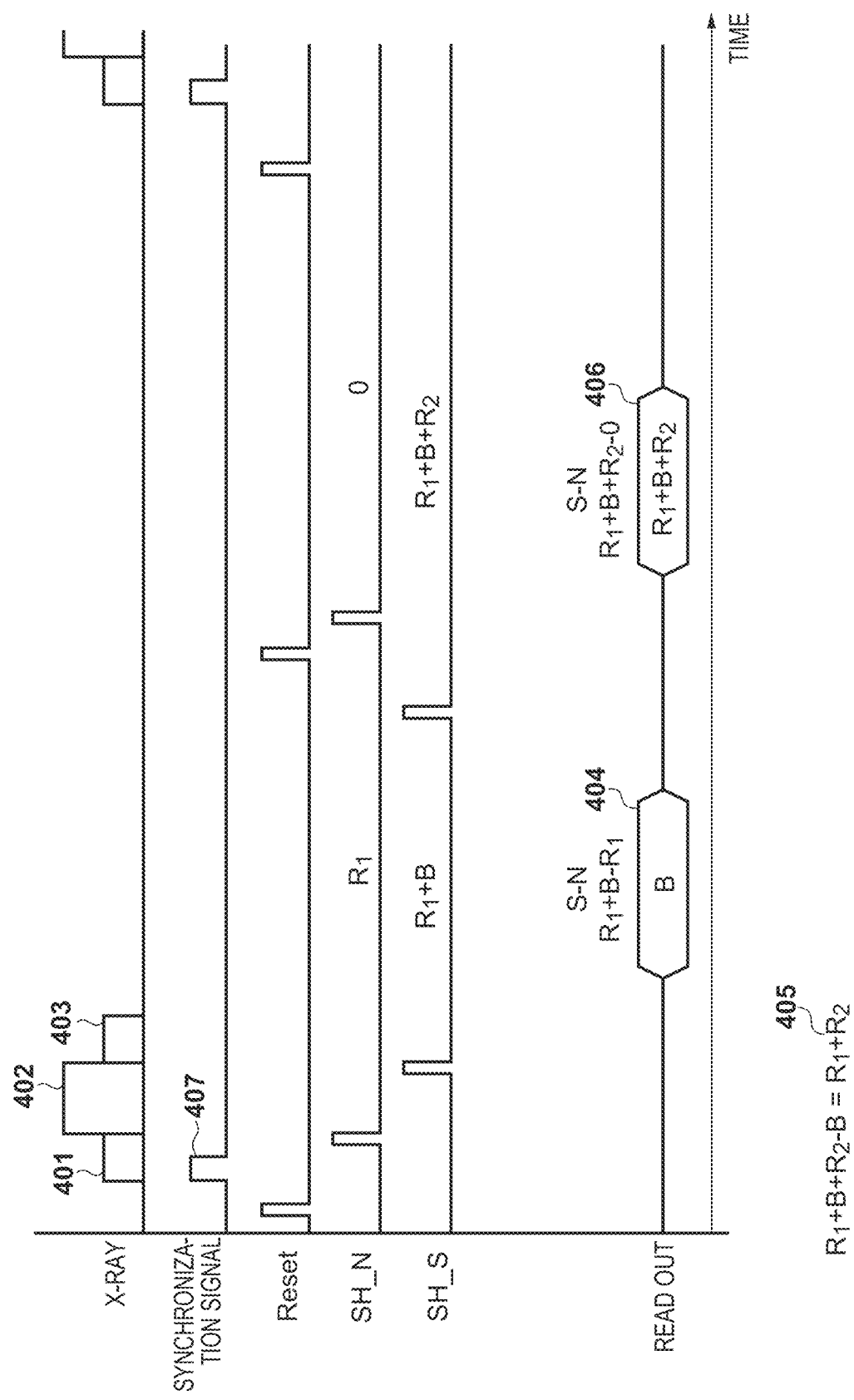

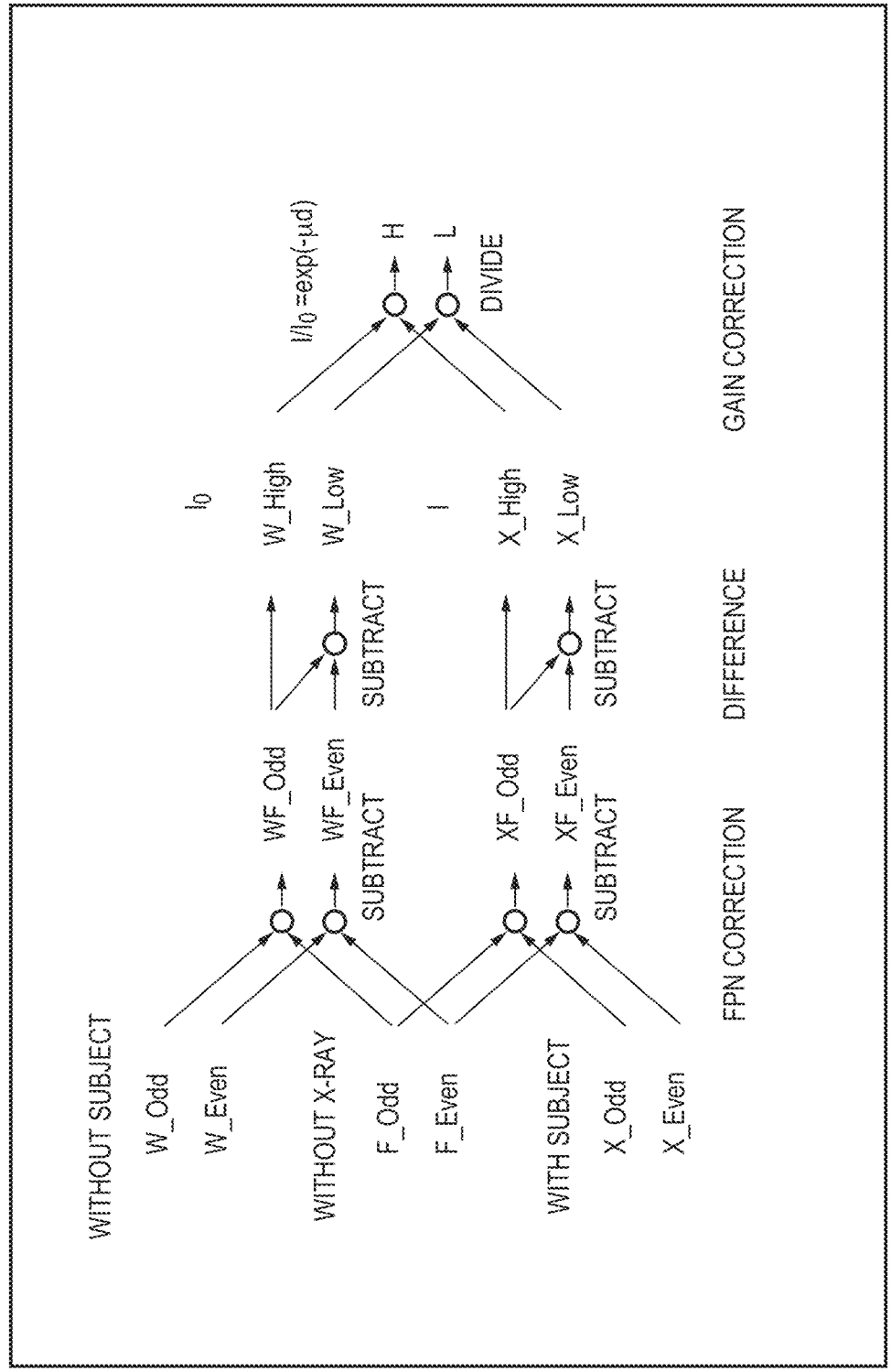

RADIATION IMAGING SYSTEM, IMAGING CONTROL APPARATUS, AND METHOD

CROSS-REFERENCE TO RELATED APPLICATIONS

This application is a Continuation of International Patent Application No. PCT/JP2019/003593, filed Feb. 1, 2019, which claims the benefit of Japanese Patent Application No. 2018-052916, filed Mar. 20, 2018, both of which are hereby incorporated by reference herein in their entirety.

BACKGROUND OF THE INVENTION

Field of the Invention

The present invention relates to a radiation imaging system and an imaging control apparatus and method.

Background Art

At present, radiation imaging apparatuses that use a flat panel detector (hereinafter, abbreviated as "FPD") made from a semiconductor material are in widespread use as radiographing apparatuses used in medical image diagnosis and non-destructive inspection that are based on radiation. Such radiation imaging apparatuses are used as digital imaging apparatuses for still image radiographing such as general radiographing and moving image radiographing such as fluorography, for example, in medical image diagnosis.

Angiography in which imaging is performed while injecting a contrast agent and endovascular treatment in which a medical device such as a catheter or a stent is used have been actively performed as moving image radiographing that uses an FPD. Methods for such angiography include digital subtraction angiography(hereinafter, referred to as "DSA"). In DSA, before a contrast agent is injected, imaging is performed and a mask image is obtained, and then after a contrast agent is injected, imaging is performed and a live image is obtained. It is possible to image only the contrast agent, and to perform vascular diagnosis, by performing computation using the mask image and the live image.

On the other hand, energy subtraction is an imaging method that uses an FPD. In energy subtraction, a plurality of images at different energies are first obtained, for example, by emitting radiation at different tube voltages a plurality of times. As a result of performing computation of these images, it is possible to perform processing such as processing for separating a bone image and a soft tissue image. Accordingly, a method for diagnosing blood vessels of a moving target by imaging only a contrast agent has been proposed (Patent Document 1).

CITATION LIST

Patent Literature

PTL1: Japanese Patent Laid-Open No. S58-221580

When DSA is applied using images generated in Patent Document 1, and if there is a moving object (e.g., a stent or a calcified substance) in a mask image, an artifact is created when the difference between a live image and the mask image is taken.

SUMMARY OF THE INVENTION

According to one aspect of the present invention, there is provided an imaging control apparatus comprising: an obtaining unit configured to obtain a plurality of images at different radiation energies, the images having been obtained as a result of irradiating a subject with radiation whose energy changes during one shot, and detect, a plurality of times, the radiation that has passed through the subject during the one shot; a first generation unit configured to generate an energy subtraction image by performing energy subtraction processing using a plurality of images; and a second generation unit configured to generate a difference image using a plurality of energy subtraction images generated by the first generation unit.

According to another aspect of the present invention, there is provided an imaging control apparatus characterized by comprising: an obtaining unit configured to obtain a first image and a second image at different radiation energies during an imaging period of one frame, as a result of a two-dimensional detector performing sampling at least twice during a period between two consecutive resets; a first generation unit configured to generate an energy subtraction image by performing energy subtraction processing on the first image and the second image; and a second generation unit configured to generate a difference image using a plurality of energy subtraction images.

According to another aspect of the present invention, there is provided an imaging control method for radiography, comprising: obtaining a plurality of images at different radiation energies, the images having been obtained as a result of irradiating a subject with radiation whose energy changes during one shot, and detecting, a plurality of times, the radiation that has passed through the subject during the one shot; generating an energy subtraction image by performing energy subtraction processing using a plurality of images; and generating a difference image using a plurality of generated energy subtraction images.

According to another aspect of the present invention, there is provided an imaging control method for radiography, comprising: obtaining a first image and a second image at different radiation energies during an imaging period of one frame, as a result of a two-dimensional detector performing sampling at least twice during a period between two consecutive resets; generating an energy subtraction image by performing energy subtraction processing on the first image and the second image; and generating a difference image using a plurality of energy subtraction images.

According to another aspect of the present invention, there is provided a radiation imaging system comprising: an imaging control apparatus comprising: an obtaining unit configured to obtain a plurality of images at different radiation energies, the images having been obtained as a result of irradiating a subject with radiation whose energy changes during one shot, and detect, a plurality of times, the radiation that has passed through the subject during the one shot; a first generation unit configured to generate an energy subtraction image by performing energy subtraction processing using a plurality of images; and a second generation unit configured to generate a difference image using a plurality of energy subtraction images generated by the first generation unit; a radiation imaging apparatus that includes a two-dimensional detector; and a radiation generation apparatus that generates radiation.

According to another aspect of the present invention, there is provided a non-transitory computer-readable storage medium storing a program for causing a computer to execute an imaging control method for radiography, the method comprising: obtaining a plurality of images at different radiation energies, the images having been obtained as a result of irradiating a subject with radiation whose energy changes during one shot, and detecting, a plurality of times, the radiation that has passed through the subject during the one shot; generating an energy subtraction image by performing energy subtraction processing using a plurality of images; and generating a difference image using a plurality of generated energy subtraction images.

According to another aspect of the present invention, there is provided a non-transitory computer-readable storage medium storing a program for causing a computer to execute an imaging control method for radiography, the method comprising: obtaining a first image and a second image at different radiation energies during an imaging period of one frame, as a result of a two-dimensional detector performing sampling at least twice during a period between two consecutive resets; generating an energy subtraction image by performing energy subtraction processing on the first image and the second image; and generating a difference image using a plurality of energy subtraction images.

Further features of the present invention will become apparent from the following description of exemplary embodiments with reference to the attached drawings.

BRIEF DESCRIPTION OF THE DRAWINGS

FIG. 3 is a timing chart showing processing for obtaining images at different radiation energies through time division.

FIG. 4 is a timing chart showing processing for obtaining images at different radiation energies through time division.

FIG. 5 is a diagram illustrating processing for correcting a radiation image.

DESCRIPTION OF THE EMBODIMENTS

Embodiments of the present invention will be described below in detail with reference to the drawings. Note that, in the embodiments below, the term "radiation" may include α-rays, β-rays, γ-ray particle beams, cosmic rays, and the like, as well as x-rays.

First Embodiment

Figure 1A:
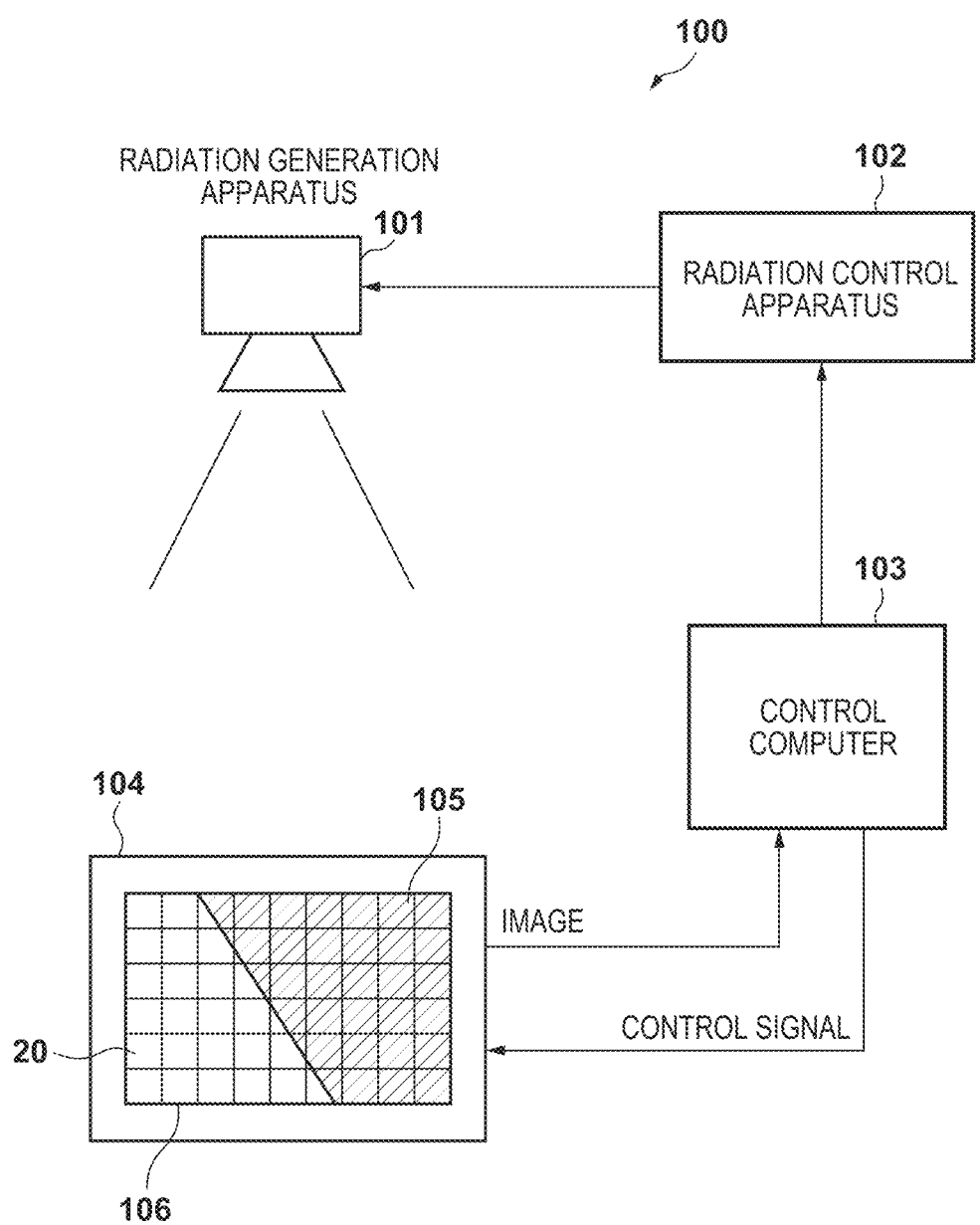
FIG. 1A is a block diagram showing a configuration example of a radiation imaging system according to an embodiment of the present invention.

FIG. 1A is a block diagram showing a configuration example of a radiation imaging system 100 according to a first embodiment. The radiation imaging system 100 according to the first embodiment includes a radiation generation apparatus 101, a radiation control apparatus 102, a control computer 103, and a radiation imaging apparatus 104.

The radiation generation apparatus 101 generates radiation under control of the radiation control apparatus 102. The control computer 103 functions as an imaging control apparatus that controls the radiation control apparatus 102 so as to irradiate radiation, and controls the radiation imaging apparatus 104 so as to obtain image information. The control computer 103 includes, for example, one or more processors (CPUs, not illustrated) and a memory, and executes various types of processing as a result of the one or more processors executing a program stored in the memory. The radiation imaging apparatus 104 includes a fluorescent body 105 that converts radiation into visible light, and a two-dimensional detector 106 that detects visible light. The two-dimensional detector 106 is a sensor in which pixels 20 for detecting radiation quanta are arranged in an array of X columns Y rows, and outputs image information.

Figure 2:
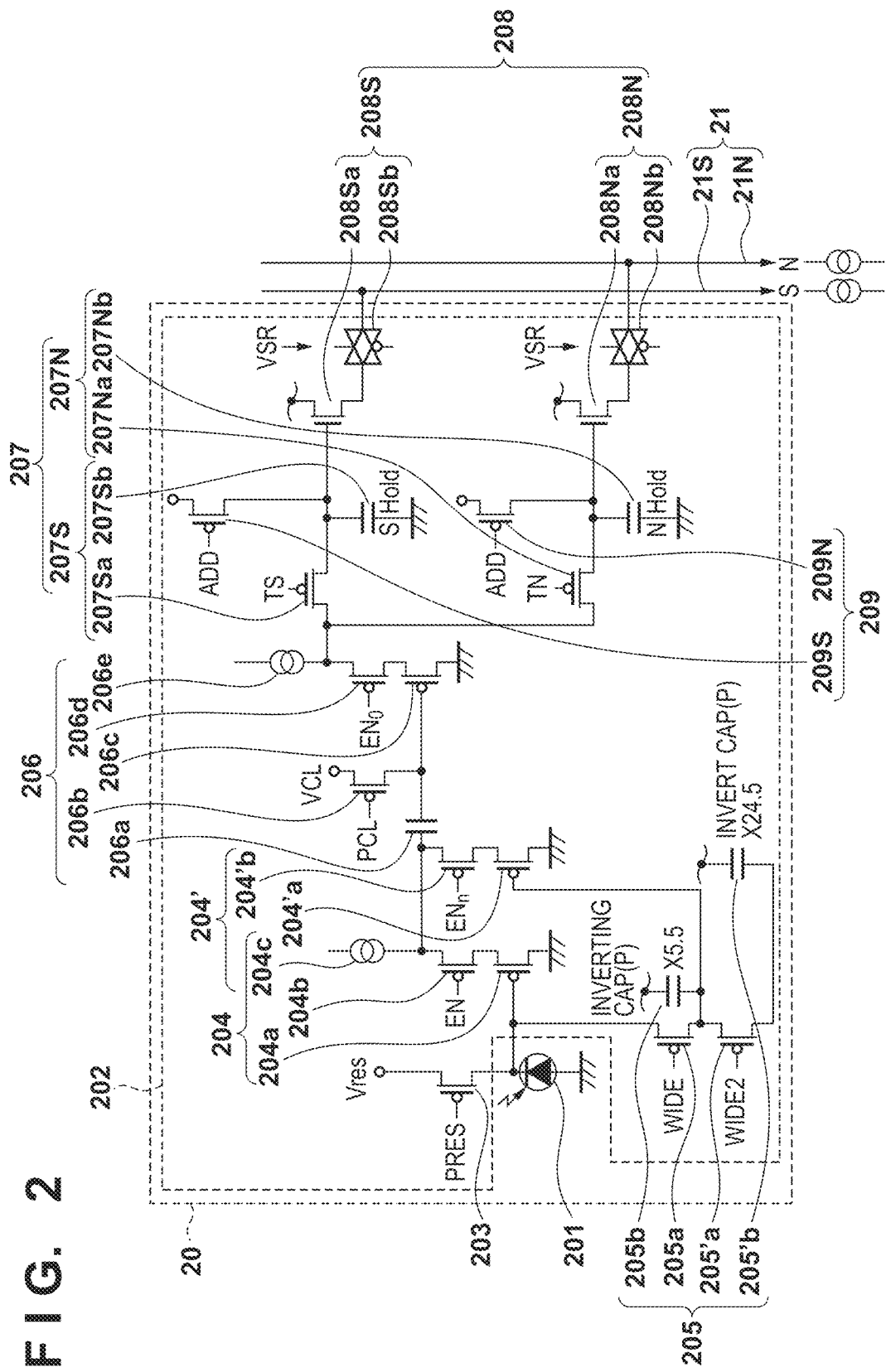
FIG. 2 is an equivalent circuit diagram of a pixel in a radiation imaging apparatus according to an embodiment of the present invention.

FIG. 2 shows an equivalent circuit diagram of a pixel 20 according to the first embodiment. Each pixel 20 includes a photoelectric conversion element 201 and an output circuit unit 202. The photoelectric conversion element 201 is typically a photodiode. The output circuit unit 202 includes an amplification circuit 204, a clamp circuit unit 206, a sample and hold circuit unit 207, and a selection circuit unit 208.

The photoelectric conversion element 201 includes a charge accumulator. This charge accumulator is connected to the gate of a MOS transistor 204a of the amplification circuit unit 204. The source of the MOS transistor 204a is connected to a current source 204c via a MOS transistor 204b. The MOS transistor 204a and the current source 204c constitute a source follower circuit. The MOS transistor 204b is an enabling switch that is switched on, and causes the source follower circuit to operate, when an enable signal EN that is supplied to the gate of the MOS transistor 204b is turned to an active level.

In the example shown in FIG. 2, the charge accumulator of the photoelectric conversion element 201 and the gate of the MOS transistor 204a constitute a common node, and this node functions as a charge-voltage converter that converts charges accumulated in the charge accumulator into a voltage. Accordingly, the charge-voltage converter exhibits a voltage V (=Q/C) that is determined based on charges Q accumulated in the charge accumulator and a capacitance value C of the charge-voltage converter. The charge-voltage converter is connected to a reset potential Vres via a reset switch 203. When a reset signal PRES is turned to an active level, the reset switch 203 is switched on, and the potential of the charge-voltage converter is reset to the reset potential Vres.

The clamp circuit unit 206 clamps noise that is output by the amplification circuit unit 204, using a clamp capacitor 206a, in accordance with the reset potential of the charge-voltage converter. Accordingly, the clamp circuit unit 206 is a circuit for cancelling noise of a signal output from the source follower circuit according to charges generated in the photoelectric conversion element 201 through photoelectric conversion. This noise includes kTC noise during resetting. Clamping is performed by setting a clamp signal PCL to an active level and switching a MOS transistor 206b to an on-state, and then setting the clamp signal PCL to a non-active level and switching the MOS transistor 206b to an off state. The output side of the clamp capacitor 206a is connected to the gate of a MOS transistor 206c. The source of the MOS transistor 206c is connected to a current source 206e via a MOS transistor 206d. The MOS transistor 206c and the current source 206e constitute a source follower circuit. The MOS transistor 206d is an enabling switch that is switched on, and causes the source follower circuit to operate, when an enable signal $EN_0$ that is supplied to the gate of the MOS transistor 206d is turned to an active level.

A signal that is output from the clamp circuit 206 according to charges generated in the photoelectric conversion element 201 through photoelectric conversion is written as an optical signal to a capacity 207Sb via a switch 207Sa as a result of an optical signal sampling signal TS being turned to an active level. A signal that is output from the clamp circuit unit 206 when the MOS transistor 206b is switched on immediately after the potential of the charge-voltage converter is reset is a clamp voltage. A noise signal is written to a capacity 207Nb via a switch 207Na as a result of a noise sampling signal TN being turned to an active level. This noise signal includes an offset component of the clamp circuit unit 206. The switch 207Sa and the capacity 207Sb constitute a signal sample and hold circuit 207S, and the switch 207Na and the capacity 207Nb constitute a noise sample and hold circuit 207N. As described above, the sample and hold circuit unit 207 includes the signal sample and hold circuit 207S and the noise sample and hold circuit 207N.

A signal line 21 includes a signal line 21S and a signal line 21N. When a drive circuit unit drives a row selection signal to an active level, a signal (optical signal) held in the capacity 207Sb is output to the signal line 21S via a MOS transistor 208Sa and a row selection switch 208Sb. Also, at the same time, a signal (noise) held in the capacity 207Nb is output to the signal line 21N via a MOS transistor 208Na and a row selection switch 208Nb. The MOS transistor 208Sa and a constant current source (not illustrated) provided on the signal line 21S constitute a source follower circuit. Similarly, the MOS transistor 208Na and a constant current source (not illustrated) provided on the signal line 21N constitute a source follower circuit. The MOS transistor 208Sa. and the row selection switch 208Sb constitute a selection circuit unit 208S for signals, and the MOS transistor 208Na and the row selection switch 208Nb constitute a selection circuit unit 208N for noise. The selection circuit unit 208 includes the selection circuit unit 208S for signals and the selection circuit unit 208N for noise.

Each pixel 20 may also include an addition switch 209S for adding optical signals of a plurality of adjacent pixels 20. In an addition mode, an addition mode signal ADD is turned to an active level, and the addition switch 209S is switched to an ON state. Accordingly, the capacities 207Sb of the adjacent pixels 20 are connected to each other by the addition switch 209S, and optical signals are averaged, Similarly, each pixel 20 may include an addition switch 209N for adding noise of a plurality of adjacent pixels 20. When the addition switch 209N is switched to an ON state, the capacities 207Nb of the adjacent pixels 2C) are connected to each other by the addition switch 209N, and noise is averaged. An adder 209 includes the addition switch 209S and the addition switch 209N.

Each pixel 20 may also include a sensitivity change unit 205 for changing the sensitivity. The pixel 20 may include, for example, a first sensitivity change switch 205a and a second sensitivity change switch 205'a as well as circuit elements ccompanying these switches. When a first change signal WIDE is turned to an active level, the first sensitivity change switch 205a is switched on, and the capacitance value of a first additional capacity 205b is added to the capacitance value of the charge-voltage converter. Accordingly, the sensitivity of the pixel 20 decreases. When a second change signal WIDE2 is turned to an active level, the second sensitivity change switch 205'a is switched on, and the capacitance value of a second additional capacity 205'b is added to the capacitance value of the charge-voltage converter. Accordingly, the sensitivity of the pixel 20 further decreases. As a result of adding a function of decreasing the sensitivity of the pixel 20 in this manner, a larger amount of light can he received, and the dynamic range can be widened. A configuration may also be adopted in which, when the first change signal WIDE is turned to the active level, an enable signal $EN_n$ is changed to the active level, and a MOS transistor 204'a, in place of the MOS transistor 204a, operates as a source follower. A MOS transistor 204'b is an enabling switch that is switched on, and causes the source follower circuit to operate, when the enable signal $EN_n$ that is supplied to the gate of the MOS transistor 204'b is turned to the active level.

Figure 1B:
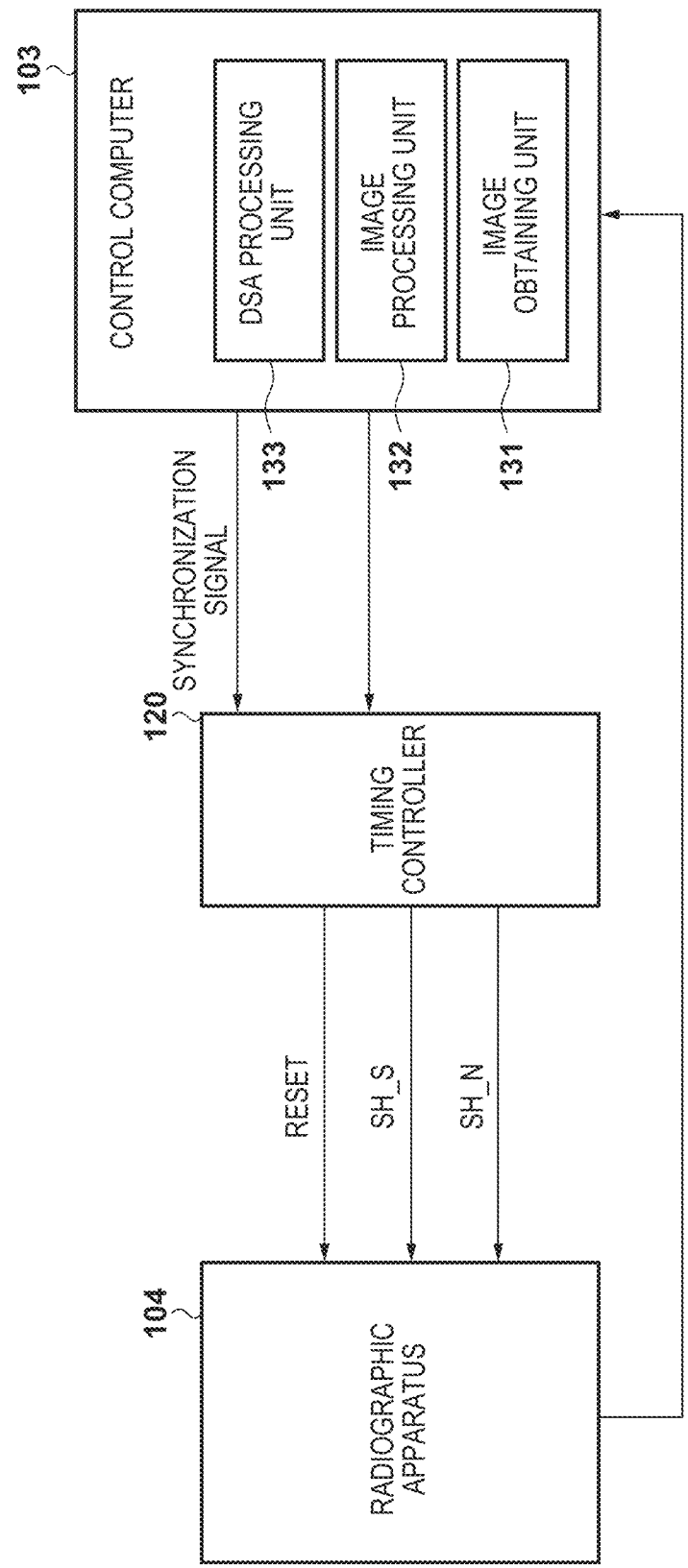
FIG. 1B is a diagram showing a functional configuration of a control computer and signals that are supplied to a radiation imaging apparatus.

The radiation imaging apparatus 104 causes an A/D converter (not illustrated) to convert output of pixel circuits that have been described above into digital values, and then transfers the digital values as an image to the control computer 103. The control computer 103 that functions as an imaging control apparatus includes an image obtaining unit 131, an image processing unit 132, and a DSA processing unit 133, as shown in FIG. 1B. Those units may be realized as a result of the processor executing a program, or some or all of those units may also be realized by dedicated hardware. The image obtaining unit 131, the image processing unit 132, and the DSA processing unit 133 will be apparent in detail in the following description. A timing controller 120 provides RESET, SH_S, and SH_N to the radiation imaging apparatus 104 in accordance with a synchronization signal from the control computer 103. Note that the RESET signal corresponds to the reset signal PRES in FIG. 2, and the SH_S signal and the SH_N signal respectively correspond to the optical signal sampling signal TS and the noise sampling signal TN in FIG. 2.

Next, driving of the radiation imaging system 100 according to the first embodiment will be described. The image obtaining unit 131 of the control computer 103 obtains a plurality of images at different radiation energies, the images have been obtained as a result of irradiating a subject with radiation whose energy changes during one shot, and detecting, a plurality of times, the radiation that has passed through the subject during the one shot. According to this embodiment, at least two sets of sampling are performed during a period between two consecutive resets using the two-dimensional detector 106, and a first image and a second image at different radiation energies are obtained during an imaging period of one frame. FIG. 3 is a timing chart showing driving timings (timings for sampling and readout) of the two-dimensional detector 106 when energy subtraction is performed in the radiation imaging system according to the first embodiment. The waveforms in the figure, in which the horizontal axis indicates time, indicate emission of radiation, a synchronization signal, reset of the photoelectric conversion element 201, the sample and hold circuit 207, and timings for reading out an image from the signal line 21. The signals (Reset, SH_S, and SH_N) shown in FIG. 3 may be supplied from the timing controller 120 shown in FIG. 1B, for example. Note that the timing controller 120 may be incorporated in the control computer 103, may also be incorporated in the radiation imaging apparatus 104, or may also be an independent apparatus disposed between the control computer 103 and the radiation imaging apparatus 104. The difference between signals (S–N) held in the signal sample and hold circuit 207S and the noise sample and hold circuit 207N is read out from the two-dimensional detector 106.

First, the photoelectric conversion element 201 is reset, and radiation is then irradiated. A tube voltage of radiation ideally has a rectangular waveform, but it requires a finite period of time for the tube voltage to rise and fall. Particularly in a case of pulse radiation that is emitted for a short time, the tube voltage can be no longer regarded as having a rectangular wave, and exhibits a waveform as shown in FIG. 3. Specifically, the energy of radiation varies for a rising period, a stable period, and a falling period of the radiation.

In view of this, after radiation 301 of a rising period is irradiated, the noise sample and hold circuit 207N performs sampling, and, furthermore, after radiation 302 of a stable period is irradiated, the signal sample and hold circuit 207S performs sampling. The difference between the signal line 21N and the signal line 21S is then read out as an image. At this time, a signal ($R_1$) of the radiation 301 of the rising period is held in the noise sample and hold circuit 207N. In addition, a signal ($R_1$+B) that represents the sum of the signal ($R_1$) of the radiation 301 of the rising period and a signal (B) of the radiation 302 of the stable period is held in the signal sample and hold circuit 207S. Therefore, image obtained by subtracting the signal ($R_1$) from the signal ($R_1$+B), that is to say, an image 304 (B) corresponding to a signal of the radiation 302 of the stable period is read out.

Next, after irradiation of radiation 303 of a falling period and readout of the image 304 have completed, the signal sample and hold circuit 207S performs sampling again. An image ($R_1$+B+$R_2$) is obtained in this sampling. The photoelectric conversion element 201 is then reset, the noise sample and hold circuit 207N performs sampling again, and the difference between the signal line 21N and the signal line 21S is read out as an image. At this time, a signal (O) when radiation is not irradiated is held in the noise sample and hold circuit 207N. In addition, the sum ($R_1$+B+$R_2$) of the signals of the radiation 301 of the rising period, the radiation 302 of the stable period, and the radiation 303 of the falling period is held in the signal sample and hold circuit 207S. Therefore, an image 306 ($R_1$+B+$R_2$) corresponding to the signal of the radiation 301 of the rising period, the signal of the radiation 302 of the stable period, and the signal of the radiation 303 of the falling period is read out. An image 305 ($R_1$+$R_2$) corresponding to the sum of the radiation 301 of the rising period and the radiation 303 of the falling period is then obtained by calculating the difference between the image 306 and the image 304.

The timing controller 120 determines timings for the sample and hold circuit 207 performing sampling and for the photoelectric conversion element 201 being reset, using a synchronization signal 307 indicating that irradiation of radiation has been started by the radiation generation apparatus 101. For example, a method for detecting start of irradiation of radiation by measuring the tube current of the radiation generation apparatus 101, and determining whether or not the measured tube current (current value) exceeds a preset threshold can be used as a method for detecting start of irradiation. Alternatively, it is also possible to use a method for detecting start of irradiation by repeatedly reading out the pixels 20 after the photoelectric conversion element 201 has been reset, and determining whether or not the pixel values exceed a preset threshold. Furthermore, it is also possible to use a method in which a radiation detector that is different from the two-dimensional detector 106 is incorporated in the radiation imaging apparatus 104, and start of irradiation is detected by determining whether or not a measurement value of the radiation detector exceeds a preset threshold. In either methods, after a time designated in advance based on input of the synchronization signal 307 has elapsed, the signal sample and hold circuit 207S performs sampling, the noise sample and hold circuit 207N sampling, and the photoelectric conversion element 201 is reset.

As described above, the image 304 corresponding to the stable period of pulse radiation and the image 305 corresponding to the sum of the rising period and the falling period are obtained by the control computer 103. The energies of radiation irradiated when these two images were formed are different, and thus energy subtraction processing can be performed using these images.

FIG. 4 shows another example of driving timings when energy subtraction is performed in the radiation imaging system 100 according to the first embodiment. The driving timings in FIG. 4 are different from the driving timings shown in FIG. 3 in that a tube voltage of radiation is actively switched.

First, the photoelectric conversion element 201 is reset, and low-energy radiation 401 is then irradiated. Thereafter, the noise sample and hold circuit 207N performs sampling, the tube voltage is then switched so as to irradiate high-energy radiation 402, and the signal sample and hold circuit 207S then performs sampling. Subsequently, the tube voltage is switched to irradiate low-energy radiation 403. Furthermore, the difference between the signal line 21N and the signal line 21S is read out as an image. At this time, the signal ($R_1$) of the low-energy radiation 401 is held in the noise sample and hold circuit 207N, and the sum ($R_1$+B) of the signal of the low-energy radiation 401 and the signal of the high-energy radiation 402 is held in the signal sample and hold circuit 207S. Therefore, an image 404 (B) corresponding to the signal of the high-energy radiation 402 is read out.

Next, after irradiation of the low-energy radiation 403 and readout of the image 404 have completed, the signal sample and hold circuit 207S performs sampling again. Subsequently, the photoelectric conversion element 201 is reset, the noise sample and hold circuit 207N performs sampling again, and the difference between the signal line 21N and the signal line 21S is read out as an image. At this time, a signal (O) when radiation is not irradiated is held in the noise sample and hold circuit 207N. Also, the sum ($R_1$+B+$R_2$) of the signals of the low-energy radiation 401, the high-energy radiation 402, and the low-energy radiation 403 is held in the signal sample and hold circuit 207S. Therefore, an image 406 ($R_1$+B+$R_2$) corresponding to the signal of the low-energy radiation 401. the signal of the high-energy radiation 402. and the signal of the low-energy radiation 403 are read out. Thereafter, as a result of calculating the difference between the image 406 and the image 404, an image 405 ($R_1$+$R_2$) corresponding to the sum of the low-energy radiation 401 and the low-energy radiation 403 is obtained. A synchronization signal 407 is similar to that in FIG. 3. As a result of obtaining images while actively switching the tube voltage in this manner, it is possible to increase the difference in energy between a low-energy image and a high-energy image, compared to the method in FIG. 3.

Next, energy subtraction processing will be described. As will be described below; the image obtaining unit 131 and the image processing unit 132 perform energy subtraction processing using a plurality of images, and generates an energy subtraction image. In this embodiment, the single two-dimensional detector 106 performs at least two sets of sampling during a period between two consecutive reset operations. Accordingly, the image obtaining unit 131 obtains two images at different radiation energies during an imaging period of one frame. The image obtaining unit 131 further performs correction processing shown in FIG. 5 on the two obtained images, and obtains a first image and a second image that are attenuation rate images. The image processing unit 132 of the control computer 103 performs energy subtraction processing (signal processing shown in FIG. 6A) on the first image and second image obtained by the image obtaining unit 131, and obtains an energy subtraction image (hereinafter, a "processed image").

FIG. 5 is a diagram illustrating correction processing that is performed by the image obtaining unit 131 in energy subtraction processing according to the first embodiment. First, imaging is performed without irradiating the radiation imaging apparatus 104 with radiation, and images are obtained through driving shown in FIG. 3 or 4. At this time, two images are read out, and a first image is denoted by F_ODD, and a second image is denoted by F_EVEN, F_ODD and F_EVEN are images corresponding to fixed pattern noise (FPN) of the radiation imaging apparatus 104. Next, radiation is irradiated to the radiation imaging apparatus 104 when there is no subject, imaging is performed, and images are obtained through driving shown in FIG. 3 or 4. At this time, two images are read out, and a first image is denoted by W_ODD, and a second image is denoted by W_EVEN. W_ODD and W_EVEN are images corresponding to the sum of signals of FPN of the radiation imaging apparatus 104 and radiation.

Therefore, as a result of subtracting F_ODD from W_ODD, and F_EVEN from W_EVEN, images WF_ODD and WF_EVEN from which FPN of the radiation imaging apparatus 104 is removed are obtained. WF_ODD is, for example, an image corresponding to the radiation 302 of the stable period in FIG. 3, and WF_EVEN is an image corresponding to the sum of the radiation 301 of the rising period, the radiation 302 of the stable period, and the radiation 303 of the falling period. Therefore, as a result of subtracting WF_ODD from WF_EVEN, an image corresponding to the sum of the radiation of the rising period and the radiation of the falling period is obtained. Energy at a rising period of radiation and energy at a falling period of radiation are lower than energy at a stable period of radiation. Therefore, as a result of subtracting WF_ODD from WF_EVEN, a low-energy image W_Low for when there is no subject is obtained. Also, a high-energy image W_High for when there is no subject is obtained from WF_ODD.

Next, the radiation imaging apparatus 104 is irradiated with radiation when there is a subject, imaging is performed, and images are obtained through driving shown in FIG. 3 or 4. At this time, two images are read out while irradiation is performed a single time, and a first image is denoted by X_ODD, and a second image is denoted by X_EVEN. As a result of performing subtraction similar to that for when there is no subject, a low-energy image X_Low for when there is a subject and a high-energy image X_High for when there is a subject are obtained.

Here, letting the thickness of a subject be d, a linear attenuation coefficient of the subject be μ output of a pixel 20 when there is no subject be $I_0$, and output of the pixel 20 when there is a subject be 1, the following expression holds true.

$$I = I_0 \exp(-\mu d) \quad (1)$$

If Expression 1 is transformed, the following expression is obtained.

$$I/I_0 = \exp(-\mu d) \quad (2)$$

The right side in Expression 2 indicates the attenuation rate of the subject. Specifically, Ho indicates an image of the attenuation rate. Note that the attenuation rate of the subject takes a real number from 0 to 1.

Therefore, as a result of dividing the low-energy image X_Low when there is a subject by the low-energy image W_Low when there is no subject, an image L of an attenuation rate at low energy is obtained. Similarly, as a result of dividing the high-energy image X_High when there is a subject by the high-energy image W_High when there is no subject, an image H of an attenuation rate at high energy is obtained.

Figure 6A:
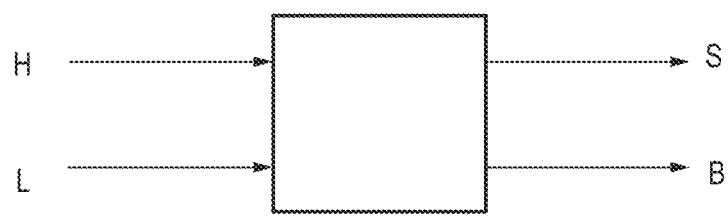
FIG. 6A is a block diagram showing signal processing related to substance separation according to a first embodiment.

FIG. 6A is a block diagram of signal processing of energy subtraction processing that is performed by the image processing unit 132. In energy subtraction processing according to this embodiment, images of a bone and soft tissue are obtained as processed images from a first image and a second image that indicate attenuation rates at two types of radiation energy. That is to say, in signal processing according to this embodiment, an image B of the thickness of a bone and an image S of the thickness of soft tissue are obtained from the image L of the attenuation rate at low energy and the image H of the attenuation rate at high energy obtained through the correction shown in FIG. S. Note that, hereinafter, the image L is also referred to as a "low-energy image", and the image H is also referred to as a "thigh-energy image".

The energy of radiation photons is indicated by E. the number of photons at the energy E is indicated by N(E), the thickness of a bone is indicated by B, the thickness of soft tissue is indicated by S, the linear attenuation coefficient of the bone at the energy E is indicated by $\mu_B(E)$, the linear attenuation coefficient of the soft tissue at the energy E is indicated by ηs(E), and the attenuation rate is indicated by $I/I_0$. Then, the following expression holds true.

$$I/I_0 = \frac{\int_0^\infty N(E)\exp\{-\mu_B(E)B - \mu_S(E)S\}EdE}{\int_0^\infty N(E)EdE} \quad (3)$$

The number of photons N(E) at the energy E is represented as a spectrum of radiation. The spectrum of radiation is obtained through simulation or actual measurement. In addition, the linear attenuation coefficient $\mu_B(E)$ of the bone at the energy E and the linear attenuation coefficient $\eta_S(E)$ of the soft tissue at the energy E are obtained from a database such as NIST. Accordingly, it is possible to calculate the attenuation rate $I/I_0$ for any thickness B of a bone, any thickness S of soft tissue, and any spectrum of radiation N(E).

Here, letting the spectrum for low-energy radiation be $N_L(E)$, and the spectrum for high-energy radiation be $N_H(E)$, the following expression holds true.

$$L = \frac{\int_0^\infty N_L(E)\exp\{-\mu_B(E)B - \mu_S(E)S\}EdE}{\int_0^\infty N_L(E)EdE} \quad (4)$$

$$H = \frac{\int_0^\infty N_H(E)\exp\{-\mu_B(E)B - \mu_S(E)S\}EdE}{\int_0^\infty N_H(E)EdE}$$

In addition, average energy $E_H$ for high-energy radiation and average energy $E_L$ for low-energy radiation are expressed as the following expression.

$$E_L = \frac{\int_0^\infty N_L(E)EdE}{\int_0^\infty N_L(E)dE} \quad (5)$$

$$E_H = \frac{\int_0^\infty N_H(E)EdE}{\int_0^\infty N_H(E)dE}$$

Here, if the spectrum of radiation N(E) is approximated as monochromatic radiation that reaches a peak for the average energy, Expression 4 can be approximated as follows.

$$L \approx \frac{N_L(E_L)\exp\{-\mu_B(E_L)B - \mu_S(E_L)S\}E_L}{N_L(E_L)E_L} = \quad (6)$$

$$\exp\{-\mu_B(E_L)B - \mu_S(E_L)S\}$$

$$H \approx \frac{N_H(E_H)\exp\{-\mu_B(E_H)B - \mu_S(E_H)S\}E_H}{N_H(E_H)E_H} =$$

$$\exp\{-\mu_B(E_H)B - \mu_S(E_H)S\}$$

If the logarithm of both sides of Expression 6 is taken, Expression 7 is obtained.

$$ln(L) \approx -\mu_B(E_L)B - \mu_S(E_L)S$$

$$ln(H) \approx -\mu_B(E_B)B - \mu_S(E_H)S \quad (7)$$

Letting a determinant when the coefficient in Expression 7 is expressed into a matrix be det, the image B of the thickness of the bone and the image S of the thickness of the soft tissue are expressed in the following expressions.

$$det = \mu_B(E_L)\mu_S(E_H) - \mu_B(E_H)\mu_S(E_L) \quad (8)$$

$$B \approx \frac{\mu_S(E_L)}{det}\ln(H) - \frac{\mu_S(E_H)}{det}\ln(L)$$

$$S \approx \frac{\mu_B(E_H)}{det}\ln(L) - \frac{\mu_B(E_L)}{det}\ln(H)$$

The linear attenuation coefficient μ(E) at the energy E takes a known value. Therefore, as a result of performing calculation of Expression 8 for all of the pixels, the image B of the thickness of the bone and the image S of the thickness of the soft tissue can be obtained from the image L of the attenuation rate at low energy and the image H of the attenuation rate at high energy. Specifically, an image ln (L) of the logarithm of the image L of the attenuation rate at low energy and an image ln (H) of the logarithm of the image H of the attenuation rate at high energy are multiplied by a coefficient that is determined based on the linear attenuation coefficient μ (E), and the difference is obtained.

Accordingly, the image B of the thickness of the bone and the image S of the thickness of the soft tissue are obtained.

Note that, according to this embodiment, the coefficient in Expression 8 is obtained based on the linear attenuation coefficients at the average energy $E_H$ and the average energy $E_L$, but this embodiment is not limited thereto. For example, the coefficient in Expression 8 may also be obtained based on a linear attenuation coefficient at energy other than average energy. In addition, the linear attenuation coefficient used in Expression 8 may also be designated by the user, or may also be inferred based on the statistics amount of an image, for example. Moreover, in the first embodiment, for ease of description, the thickness B of the bone and the thickness S of the soft tissue are calculated, but there is no limitation to such a mode. For example, the thickness W of water and the thickness I of a contrast agent may be calculated. It can be shortly said that signal processing according to the first embodiment is processing for breaking data down into thicknesses of any two types of substances.

As described above, energy subtraction is performed on a first image (H) and a second image (L), and a first processed image (B) related to the thickness of a first substance (bone) and a second processed image (S) related to the thickness of a second substance (soft tissue) that is different from the first substance are obtained. More specifically, the first processed image and the second processed image are obtained based on linear attenuation coefficients of the first substance and the second substance for first radiation energy and linear attenuation coefficients of the first substance and the second substance for second radiation energy.

The DSA processing unit 133 generates a difference image using a plurality of energy subtraction images generated by the image processing unit 132 as described above. According to this embodiment, digital subtraction angiography (hereinafter, referred to as "DSA") is used as an example of generation of a difference image. The DSA processing unit 133 generates a difference image though DSA, using processed images obtained through energy subtraction processing. The first processed images (B) before and after a contrast agent is injected are used in generation of a DSA image. That is to say, according to the first embodiment, a mask image is generated using a processed image obtained through energy subtraction processing before a contrast agent is injected. A live image is then generated using a processed image obtained through energy subtraction processing after a contrast agent is injected, and a difference image (DSA image) between the mask image and the live image is generated.

Figure 7:
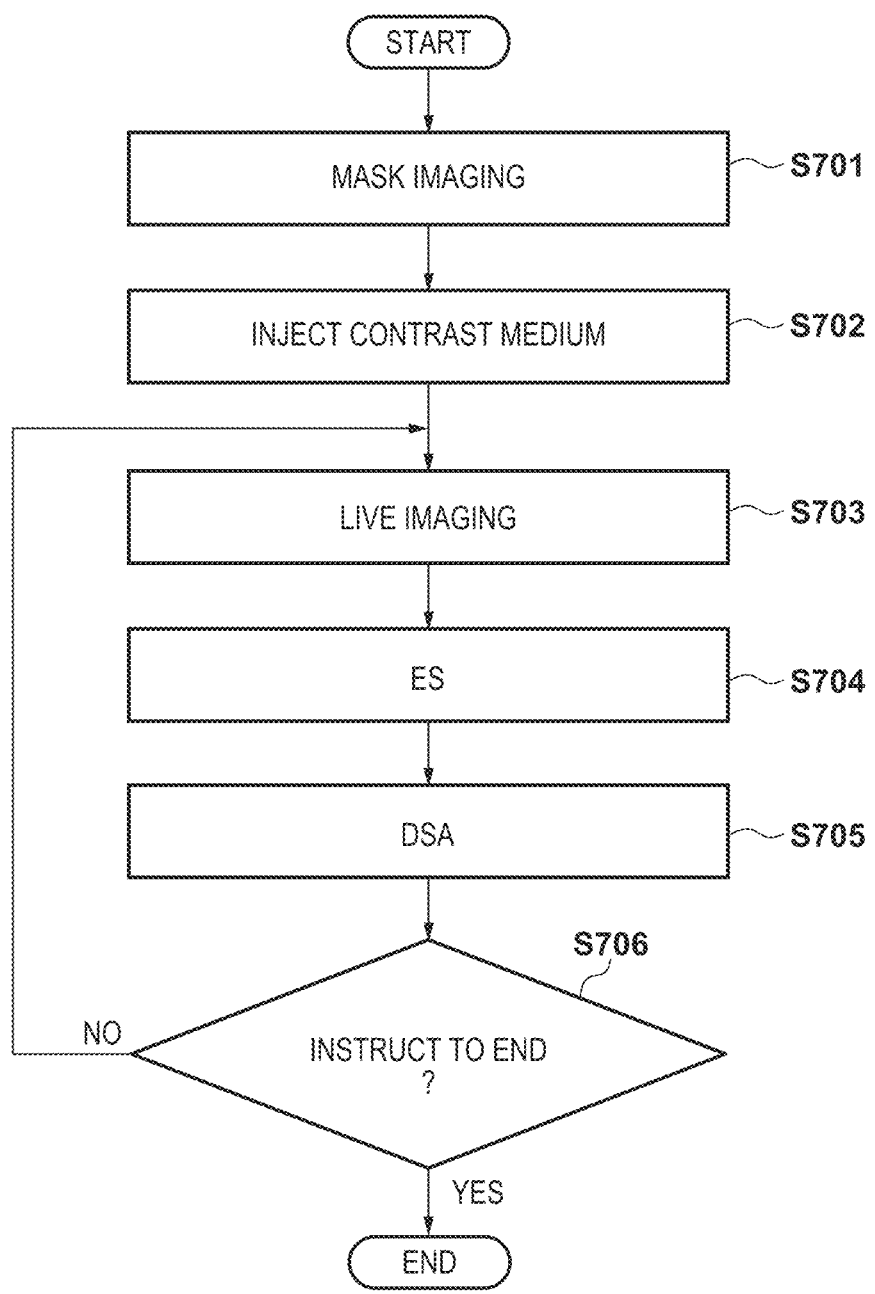
FIG. 7 is a flowchart showing processing that uses digital subtraction angiography according to the first embodiment.

FIG. 7 shows a flowchart according to the first embodiment. First, the image obtaining unit 131 obtains a high-energy mask image HM and a low-energy mask image $L_M$ by performing imaging at a timing shown in FIG. 3 or 4 before a contrast agent is injected, and performing correction shown in FIG. 5 (step S701). After a contrast agent is injected (step S702), the image obtaining unit 131 performs imaging and correction similar to those when the mask image was obtained, and obtains a live image $H_L$ at high energy and a live image $L_L$ at low energy (step S703). The image processing unit 132 then performs signal processing shown in FIG. 6A, on the high-energy mask image $H_M$ and the low-energy mask image $L_M$, and separates them into a mask image $B_M$ of the bone and a mask image $S_M$ of the soft tissue. Furthermore, the image processing unit 132 performs similar processing on the live image $H_L$ at high energy and the live image $L_L$ at low energy, and separates them into a live image $B_L$ of the bone and a live image $S_L$ of the soft tissue (step S704). The DSA processing unit 133 then obtains a DSA image $B_{DSA}$ of the bone by subtracting the mask image $B_M$ of the bone from the live image $B_L$ of the bone, and obtains a DSA image $S_{DSA}$ of the soft tissue by subtracting the mask image $S_M$ of the soft tissue from the live image $S_L$ of the soft tissue (step S705). It is possible to obtain a moving image in which energy subtraction and DSA are combined by repeating the above-described imaging of live image and image processing until an instruction to end the processing is given (NO in step S706). When an instruction to end the processing is given (YES in step S706), this processing ends.

Figure 8:
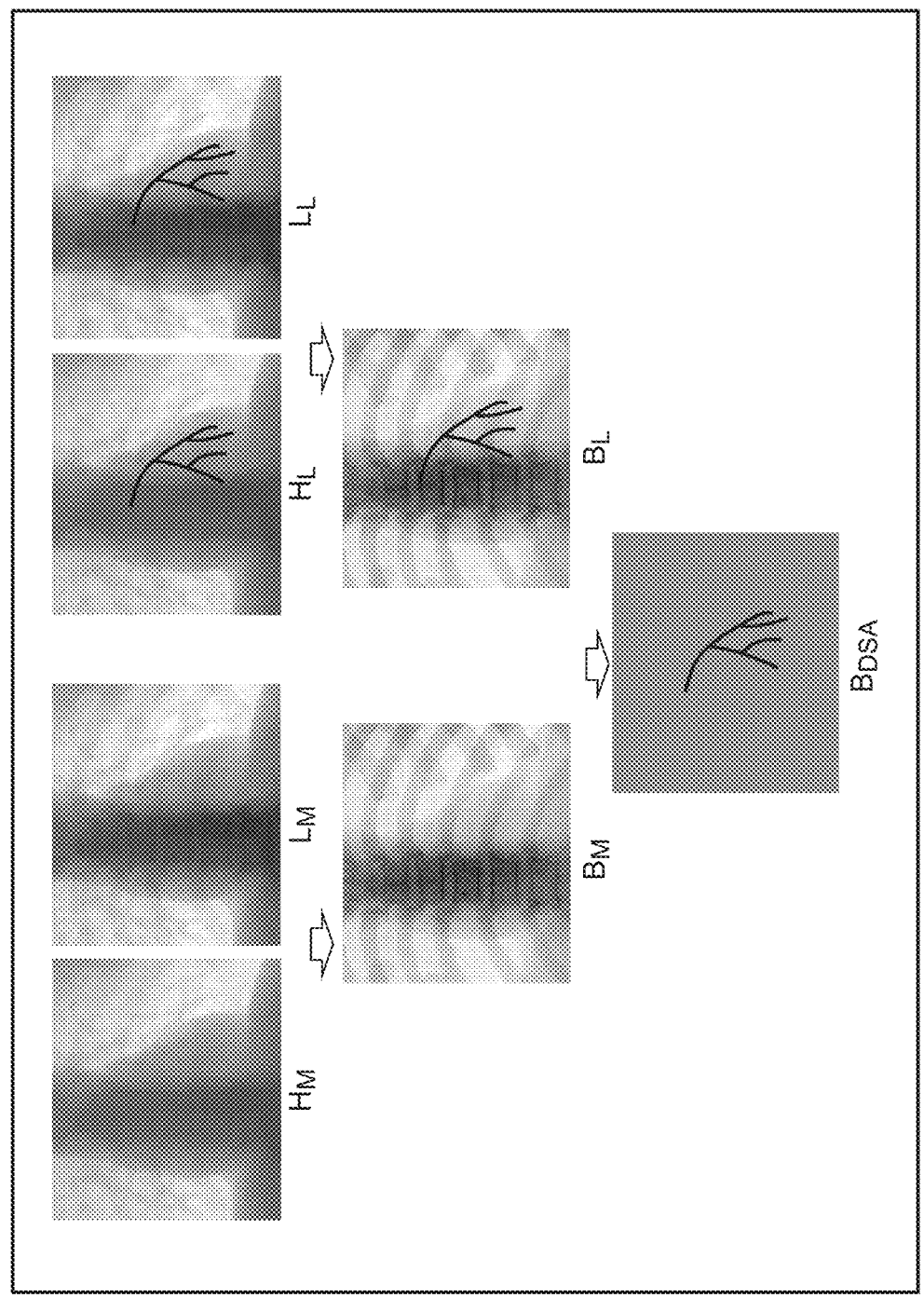
FIG. 8 is a schematic diagram illustrating processing that uses digital subtraction angiography according to the first embodiment.

FIG. 8 shows a schematic diagram of image processing according to the first embodiment. FIG. 8 shows a state where a DSA image $B_{DSA}$ is generated based on a mask image $B_M$ of bones and a live image $B_L$ of the bones. The high-energy mask image $H_M$ and the low-energy mask image LM are images imaged before a contrast agent is injected, and thus include information regarding the bones and soft tissue only. The mask image $B_M$ of the bones obtained by performing energy subtraction on these mask images includes information regarding the bones, and a mask image $S_M$ of soft tissue (not illustrated) includes information regarding the soft tissue. On the other hand, a live image $H_L$ at high energy and a live image $L_L$ at low energy are images imaged after a contrast agent was injected, and include information regarding the bones, the soft tissue, and the contrast agent. If energy subtraction is performed on these live images, information regarding the contrast agent that is a third substance appears in the live image $B_L$ of the bones. This is because the linear attenuation coefficient of the bones and the linear attenuation coefficient of the contrast agent are close. Accordingly, the live image $B_L$ of the bones includes information regarding the bones and the contrast agent, and the live image $S_L$ of the soft tissue (not illustrated) includes information regarding the soft tissue.

When an organ moves due to heartbeats, breathing, and the like between a mask image and a live image, a large change occurs in an image of soft tissue. However, the position of a bone does not change largely. Accordingly, information regarding the bone included in the live image $B_L$ of the bone and information regarding the bone included in the mask image $B_M$ of the bone are substantially the same. Therefore, in the DSA image $B_{DSA}$ of the bone, information regarding the bone is offset, and substantially only the information regarding the contrast agent remains. In this manner, even if movement occurs due to heartbeats, breathing, and the like, it is possible to image only the contrast agent, and to diagnose blood vessels.

In addition, according to the first embodiment, radiation images for high-energy and low-energy are obtained by using the sample and hold circuits as shown in FIGS. 3 and 4, but there is no limitation to such a mode. For example, a configuration may also be adopted in which, after high-energy radiation is irradiated and an image is read out, low-energy radiation is irradiated and an image is read out, and high-energy and low-energy radiation images are then obtained. However, in this embodiment, it is envisioned that the sample and hold circuits are used in a situation where a subject moves due to heartbeat, breathing, and the like. There is the issue that, when the subject moves, if there is a time difference between high-energy and low-energy radiation images, a motion artifact is created in an image after energy subtraction. For such a reason, according to this embodiment, as shown in FIGS. 3 and 4, high-energy and low-energy radiation images are imaged while one frame is imaged (before next reset is performed). Such imaging may be realized by using the sample and hold circuit units 207 of the pixels 20 of the two-dimensional detector 106. Such imaging is called time-division driving. Time-division driving makes it possible to shorten the time difference in imaging between high-energy and low-energy radiation images, and thus is a mode desirable for generation of a DSA image. Specifically, it is possible to shorten the interval of imaging for obtaining images at different energies, and to obtain a DSA image without any artifact, with high accuracy. In addition, a configuration may also be adopted in which a high-energy radiation image, a moderate-energy radiation image, and a low-energy radiation image (three or more radiation images) are obtained by using sample and hold circuits, and energy subtraction processing is performed.

According to this embodiment, in order to obtain radiation images at different energies, a method in which two FPDs are stacked, and a front-side FPD when viewed from the radiation emission side obtains a low-energy radiation image, and a back-side FPD obtains a high-energy radiation image may also be used. In this method, there is no time difference between high-energy and low-energy radiation images, and thus no motion artifact is created. However, when FPDs are stacked, radiation penetrates the front-side FPD. If this FPD is made of amorphous silicon, there is no problem, but if this FPD is made of crystalline silicon, there is a problem in that pixel circuits deteriorate due to radiation, and the image quality decreases. In angiography and endovascular treatment, radiation continues to be irradiated for a long time, and thus pixel circuits are likely to deteriorate. In addition, an FPD of crystalline silicon is more expensive than an FPD of amorphous silicon. Accordingly, stacking FPDs of crystalline silicon is unwanted in terms of the image quality and cost. On the other hand, in an FPD of amorphous silicon, offsets and afterimages are likely to occur compared with an FPD of crystalline silicon. Particularly in the case of a moving image, there is the issue that larger offsets and afterimages occur, and an artifact is created in an image after energy subtraction. For such a reason as well, imaging of high-energy and low-energy radiation images that is performed through time-division driving according to this embodiment is a more desirable mode.

In addition, driving timings for obtaining a first image and a second image at different radiation energies are not limited to driving timings shown in FIGS. 3 and 4. It suffices for the driving timing to be a driving timing at which a first image and a second image at different radiation energies can be obtained during an imaging period of one frame.

Second Embodiment

Figure 6B:
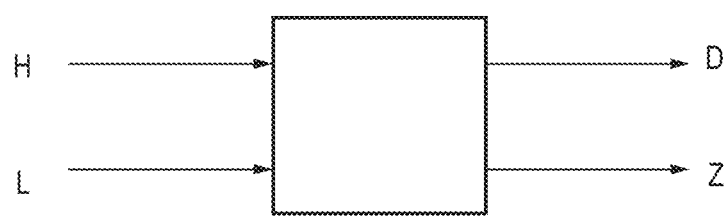
FIG. 6B is a block diagram showing signal processing related to substance identification according to a second embodiment.

According to the first embodiment, images of the thicknesses of two types of substances (for example, images of soft tissue (S) and a bone (B) in FIG. 6A) are obtained based on the radiation image (H) of the attenuation rate at high energy and the radiation image (L) of the attenuation rate at low energy. According to a second embodiment, an image of an effective atomic number (Z) and an image of an area density (D) are obtained based on a high-energy radiation image (H) and a low-energy radiation image (L) (FIG. 6B). Note that the configuration of the radiation imaging system 100 according to the second embodiment and an operation of obtaining high/low-energy radiation images are similar to those in the first embodiment (FIG. 1A to 5)

FIG. 6B is a block diagram of signal processing of energy subtraction processing that is performed by the image processing unit 132 according to the second embodiment. As described above, in signal processing according to the second embodiment, an image of an effective atomic number Z and an image of an area density D are obtained based on the image L of the attenuation rate at low energy and the image H of the attenuation rate at high energy obtained through correction processing shown in FIG. 5. Note that the effective atomic number Z is an equivalent atomic number of a mixture. Also, the area density D is the product of the density [g/cm$^3$] of a subject and the thickness of the subject [cm], and has a dimension [g/cm$^2$].

First, letting the energy of radiation photons be E, the number of photons at the energy E be N(E), an effective atomic number be Z, an area density be D, a mass attenuation coefficient for the effective atomic number Z and the energy E be μ (Z, E), and an attenuation rate be I/I$_0$, the following expression holds true.

$$I/I_0 = \frac{\int_0^\infty N(E)\exp\{-\mu(Z,E)D\}EdE}{\int_0^\infty N(E)EdE} \tag{9}$$

The number of photons N(E) at the energy E is represented as a spectrum of radiation. The spectrum of radiation is obtained through simulation or actual measurement. In addition, the mass attenuation coefficient μ (Z, E) for the effective atomic number Z and the energy E is obtained from a database such as NIST. Accordingly, it is possible to calculate the attenuation rate I/I$_0$ for any effective atomic number Z, area density D, and spectrum of radiation N(E) using Expression 9.

Here, letting a spectrum of radiation of low-energy be N$_L$(E), and a spectrum of radiation of high-energy be N$_H$(E), the following expression holds true.

$$L = \frac{\int_0^\infty N_L(E)\exp\{-\mu(Z,E)D\}EdE}{\int_0^\infty N_L(E)EdE} \tag{10}$$

$$H = \frac{\int_0^\infty N_H(E)\exp\{-\mu(Z,E)D\}EdE}{\int_0^\infty N_H(E)EdE}$$

Here, similarly to the first embodiment, if the spectrum of radiation N(E) is approximated as monochromatic radiation that reaches a peak for the average energy, Expression 10 can be approximated as follows.

$$L \approx \frac{N_L(E_L)\exp\{-\mu(Z,E_L)D\}E_L}{N_L(E_L)E_L} = \exp\{-\mu(Z,E_L)D\} \tag{11}$$

$$H \approx \frac{N_H(E_H)\exp\{-\mu(Z,E_H)D\}E_H}{N_H(E_H)E_H} = \exp\{-\mu(Z,E_H)D\}$$

if the logarithm of both sides of Expression 11 is taken, Expression 12 is obtained.

$$ln(L) \approx -\mu(Z, E_L)D$$

$$ln(H) \approx -\mu(Z, E_H)D \tag{12}$$

Furthermore, if the term of the area density is offset by taking the ratio of Expression 12, the following, expression is obtained.

$$\frac{\ln(L)}{\ln(H)} \approx \frac{-\mu(Z,E_L)D}{-\mu(Z,E_H)D} = \frac{\mu(Z,E_L)}{\mu(Z,E_H)} = f(Z) \tag{13}$$

Specifically, the ratio of the logarithms of an attenuation rate L at low enemy and an attenuation rate H at high energy is uniquely obtained based on the effective atomic number. Therefore, if an inverse function is obtained, the effective atomic number Z can be obtained based on the ratio of the logarithms of the attenuation rate L at low energy and the attenuation rate H at high energy. In addition, if the effective atomic number Z is determined, the area density D can be obtained based on Expression 12.

$$Z \approx f^{-1}\left(\frac{\ln(L)}{\ln(H)}\right) \tag{14}$$

$$D \approx \frac{-\ln(L)}{\mu(Z,E_L)}$$

As a result of performing calculation of Expression 14 for all of the pixels in this manner, an image of the effective atomic number Z and an image of the area density D can be obtained based on the image L of the attenuation rate at low energy and the image H of the attenuation rate at high energy.

Figure 6C:
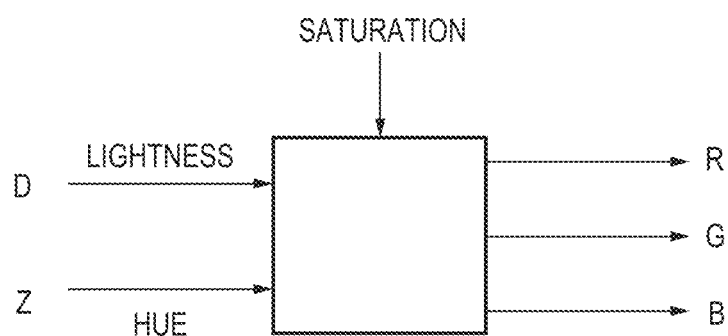
FIG. 6C is a block diagram showing image processing of color image generation according to the second embodiment.

FIG. 6C is a block diagram of image processing of energy subtraction processing according to the second embodiment. In the image processing according to the second embodiment, a color transparent image is obtained based on the image of the effective atomic number Z and the image of the area density D obtained through the signal processing shown in FIG. 6B. An HLS color space is suitably used for conversion at this time. The HLS color space is a color space composed of three components, namely hue H, saturation S, and lightness L. A configuration in which the hue H is determined based on the effective atomic number Z, and the lightness L is determined based on the area density D may be used as a method for using the HLS color space. A color radiation image generated through such image processing is used for baggage inspections at airports and the like. Note that the saturation S may be designated by the user, or a fixed value may also be used.

Examples of a method for generating a color image by converting the hue H, the saturation S, and the lightness L of the HLS color space into RGB values includes methods for using a cylindrical model and a conical model. For example, in the conical model, the following expression is used.

$$Max = L + \frac{S}{2} \tag{15}$$

$$Min = L - \frac{S}{2}$$

$$(R, G, B) = \qquad (16)$$

$$\begin{cases} (\text{Max} = \text{Min}, \text{Max} = \text{Min}, \text{Max} = \text{Min}) & \text{if } H \text{ is undefined} \\ \left(\text{Max}, \text{Min} + (\text{Max} - \text{Min}) \times \frac{H}{60}, \text{Min}\right) & \text{if } 0 \le H < 60 \\ \left(\text{Min} + (\text{Max} - \text{Min}) \times \frac{120 - H}{60}, \text{Max}, \text{Min}\right) & \text{if } 60 \le H < 120 \\ \left(\text{Min}, \text{Max}, \text{Min} + (\text{Max} - \text{Min}) \times \frac{H - 120}{60}\right) & \text{if } 120 \le H < 180 \\ \left(\text{Min}, \text{Min} + (\text{Max} - \text{Min}) \times \frac{240 - H}{60}, \text{Max}\right) & \text{if } 180 \le H < 240 \\ \left(\text{Min} + (\text{Max} - \text{Min}) \times \frac{H - 240}{60}, \text{Min}, \text{Max}\right) & \text{if } 240 \le H < 300 \\ \left(\text{Max}, \text{Min}, \text{Min} + (\text{Max} - \text{Min}) \times \frac{360 - H}{60}\right) & \text{if } 300 \le H < 360 \end{cases}$$

The saturation S takes a real number from 0 to 1. For example, if the saturation S=0, then Max=L and Min=L, and thus, whichever a value the hue H takes, the RGB values are (L, L, L). Accordingly, a monochrome image that reflects only the lightness L is obtained. In contrast, the more the saturation S approximates to 1, the more the information regarding the hue H is reflected, and thus a material that makes up the subject is easily identified based on the color. Therefore, a mode for manually adjusting the saturation S is preferable.

The processing according to the second embodiment is performed. according to a flowchart similar to that in FIG. 7. However, energy subtraction (step S704) and a DSA processing method (step S705) are different. First, the image obtaining unit 131 obtains a high-energy mask image $H_M$ and a low-energy mask image $L_M$ by performing imaging at the timing shown in FIG. 3 or 4 before a contrast agent is injected, and performing correction shown in FIG. 5. Next, after a contrast agent is injected, the image obtaining unit 131 performs imaging and correction similar to those described above, and obtains a live image HL at high energy and a live image $L_L$ at low energy. Subsequently, the image processing unit 132 performs signal processing shown in FIG. 6B on the high-energy mask image $H_M$ and the low-energy mask image $L_M$, and separates them into a mask image $Z_M$ of an effective atomic number and a mask image $D_M$ of an area density. Furthermore, the image processing unit 132 performs similar processing on the live image $H_L$ at high energy and the live image $L_L$ at low energy as well, and separates them into a live image $Z_L$ of an effective atomic number and a mask image $D_L$ of an area density. At this time, the relationship between the images is represented by Expression 17 below.

$$D_L = D_M + D_{DSA} \qquad (17)$$

$$Z_L^n * \frac{D_L}{D_L} = Z_M^n * \frac{D_M}{D_L} + Z_{DSA}^n * \frac{D_{DSA}}{D_L}$$

Here, n is a real number larger than or equal to 2.5 and smaller than or equal to 3, and, for example, n=2.94. If this expression is transformed, Expression 18 below is obtained.

$$D_{DSA} = D_L - D_M \qquad (18)$$

$$Z_{DSA} = \sqrt[n]{Z_L^n * \frac{D_L}{D_{DSA}} - Z_M^n * \frac{D_M}{D_{DSA}}}$$

The DSA processing unit 133 obtains a DSA image $D_{DSA}$ of an area density and a DSA image $Z_{DSA}$ of an effective atomic number using Expression 18. That is to say, a DSA image of an effective atomic number is obtained based on a mask image and a live image of an area density ($D_M$ and $D_L$) and a mask image and a live image ($Z_M$ and $Z_L$) of an effective atomic number. Note that the DSA image $Z_{DSA}$ of an effective atomic number may also be obtained by simply subtracting the mask image $Z_M$ of an effective atomic number from the live image $Z_L$ of an effective atomic number, or the like. Lastly, a color DSA image $C_{DSA}$ is obtained by performing image processing in FIG. 10 on the DSA image $D_{DSA}$ of the area density and the DSA image $Z_{DSA}$ of the effective atomic number. As a result of repeating such imaging and image processing of a live image, it is possible to obtain a color moving image in which energy subtraction and DSA are combined.

Figure 9:
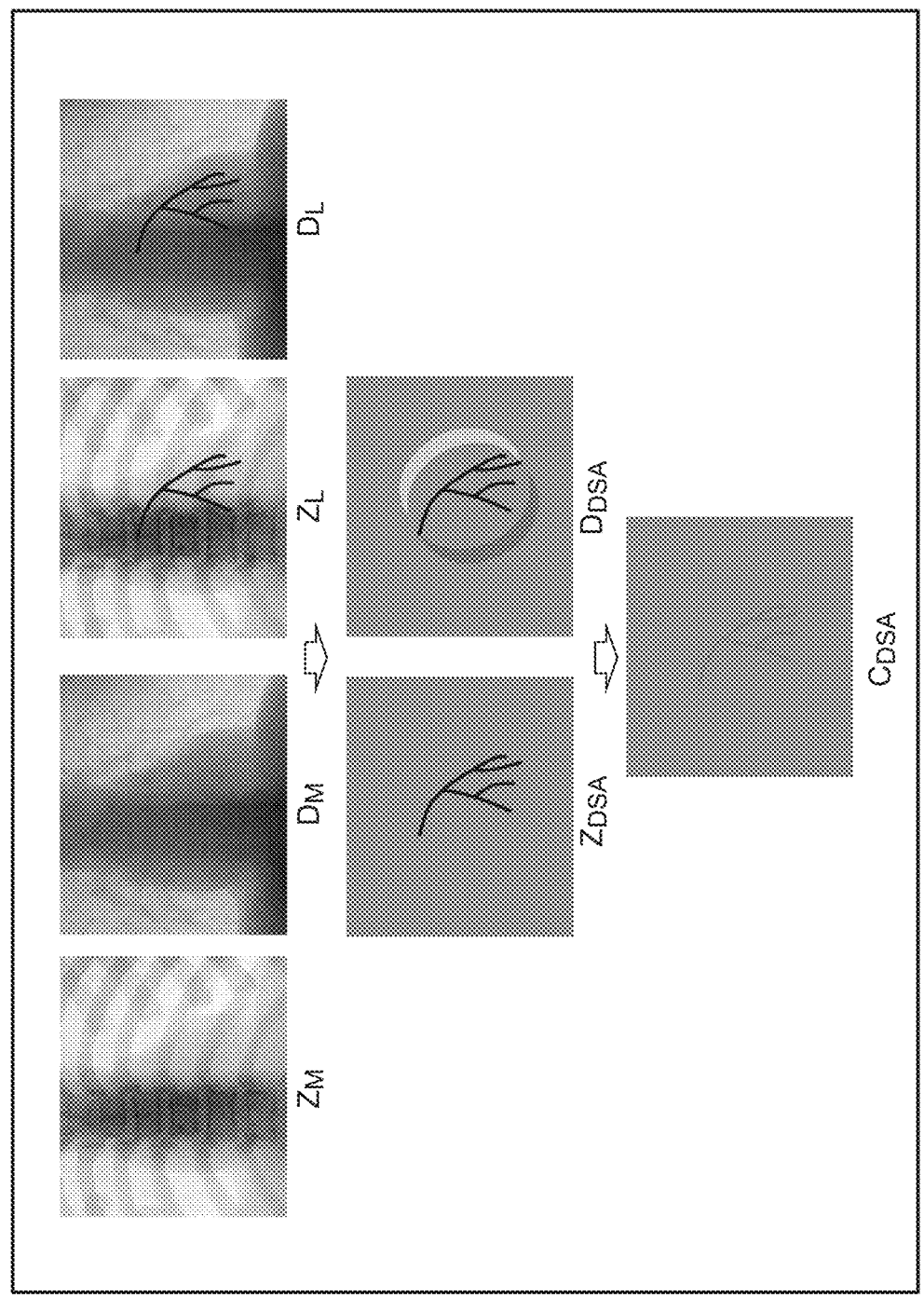
FIG. 9 is a schematic diagram illustrating processing that uses digital subtraction angiography according to the second embodiment.

FIG. 9 is a schematic diagram of image processing according to the second embodiment. Similar to FIG. 8, an organ moves due to heartbeat, breathing, and the like between a mask image and live image, but the positions of bones does not move largely. Therefore, in a portion in which the organ moved, the DSA image $D_{DSA}$ of the area density changes, but the DSA image $Z_{DSA}$ of the effective atomic number does not change largely. On the other hand, in a portion in which a contrast agent was injected, the DSA image $D_{DSA}$ of the area density and the DSA image $Z_{DSA}$ of the effective atomic number change. Therefore, in the DSA image $Z_{DSA}$ of the effective atomic number, only information regarding the contrast agent remains. This may be displayed as is.

Alternatively, a new DSA image may also be generated using the DSA image $Z_{DSA}$ of the effective atomic number and the DSA image $D_{DSA}$ of the area density. In this case, for example, processing for setting thresholds for the respective pixel values of the DSA image $Z_{DSA}$ of the effective atomic number and the DSA image $D_{DSA}$ of the area density, and if a pixel value is smaller than a threshold, clipping the pixel value to 0, then multiplying the pixel values, and the like is suitably used. Furthermore, the color DSA image $C_{DSA}$ obtained by performing image processing in FIG. 6C may also be generated. in either cases, both a change in the area density and a change in the effective atomic number are used, and thus only the contrast agent can be more accurately imaged. in this manner, even if movement occurs due to heartbeats, breathing, and the like, it is possible to image only the contrast agent, and to diagnose blood vessels.

In addition, in the DSA image $Z_{DSA}$ of the effective atomic number according to the second embodiment, a change in the effective atomic number caused by soft tissue and bones is removed by subtracting the mask image. Therefore, it is possible to measure the effective atomic number (type) of a substance inserted after the mask image was obtained. Accordingly, there is an advantage that a contrast agent (iodine), a catheter, and a stent (iron) can be identified using the effective atomic number. In addition, regarding a portion in which the position of a bone is slightly deviates due to breathing or the like, it is considered that bone was added after the mask image was obtained. Therefore, it is also possible to perform processing for identifying the contrast agent (iodine) and the bone (calcium) using the effective atomic number, and imaging only the contrast agent, and the like.

Note that, in generation of a DSA image using images of an effective atomic number and an area density, to use time-division driving in order to obtain images of attenuation rates for two different radiation energies is a preferred embodiment, but there is no limitation thereto. For example, as described above in the first embodiment, images of attenuation rates for two different radiation energies may also be obtained using a method other than that of time-division driving.

Third Embodiment

According to the first and second embodiments, imaging is performed and a mask image is generated, before a contrast agent is injected. According to a third embodiment, a mask image is generated based on a processed image of a plurality of frames earlier than the current frame from among processed images obtained through energy subtraction processing. A DSA image that is a difference image between a mask image and a live image, which is a processed image of the current frame, is then generated. More specifically, the image processing unit 132 performs energy subtraction processing using a plurality of images at different radiation energies, and generates an energy subtraction image. The DSA processing unit 133 generates a difference image between a mask image that is based on a plurality of energy subtraction images generated in the past and a live image that is based on the current energy subtraction image. Note that the configuration and operations of the radiation imaging system 100 according to the third embodiment are similar to those in the first and second embodiments. The third embodiment will be described below in detail.

Figure 10:
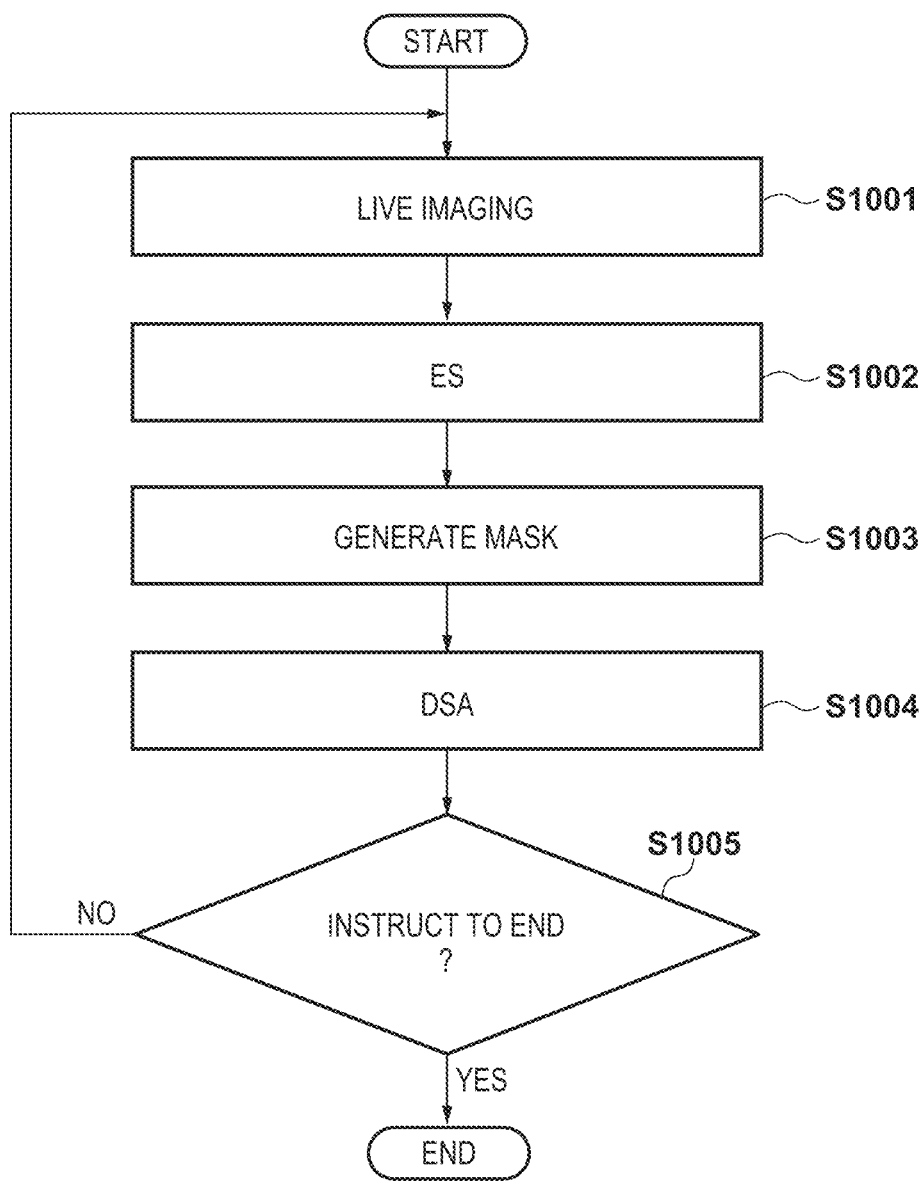
FIG. 10 is a flowchart showing processing that uses digital subtraction angiography according to a third embodiment.

FIG. 10 is a flowchart according to the third embodiment. Unlike the first embodiment, no mask image is imaged, and whether or not a contrast agent is injected is not questioned. First, the image obtaining unit 131 obtains a live image $H_L$ at high energy and the live image $L_L$ at low energy (step S1001). Subsequently, the image processing unit 132 performs signal processing shown in FIG. 6A on the live image $H_L$ at high energy and the live image $L_L$ at low energy, and separates them into a live image $B_L$ of a bone and a live image $S_L$ of soft tissue (step S1002). As a result of repeating such imaging and energy subtraction processing of live images, a moving image is obtained.

Here, a live image of a bone of the current frame is denoted by $B_L[0]$ and a live image of the bone of an n-th frame before the current frame is dented by $B_L[-n]$. Note that n is an integer of 2 or larger. The DSA processing unit 133 generates a mask image $B_M$ of the bone using n images from the live image $B_L[-n]$ of the bone of the n-th frame before the current frame to a live image $B_L[-1]$ of the bone of the first frame before the current frame (step S1003). Lastly, the DSA processing unit 133 obtains a DSA image $B_{DSA}$ of the bone by subtracting the mask image $B_M$ of the bone from the live image $B_L$ of the bone, in which the live image $B_L[0]$ of the bone of the current frame is used as the live image $B_L$ of the bone (step S1004). Also regarding soft tissue, a DSA image $S_{DSA}$ of soft tissue can be obtained by subtracting a mask image $S_M$ of the soft tissue from a live image $S_L$ of the soft tissue similarly. As a result of repeating such imaging and image processing of live images, a moving image in which energy subtraction and DSA are combined is obtained.

Figure 11:
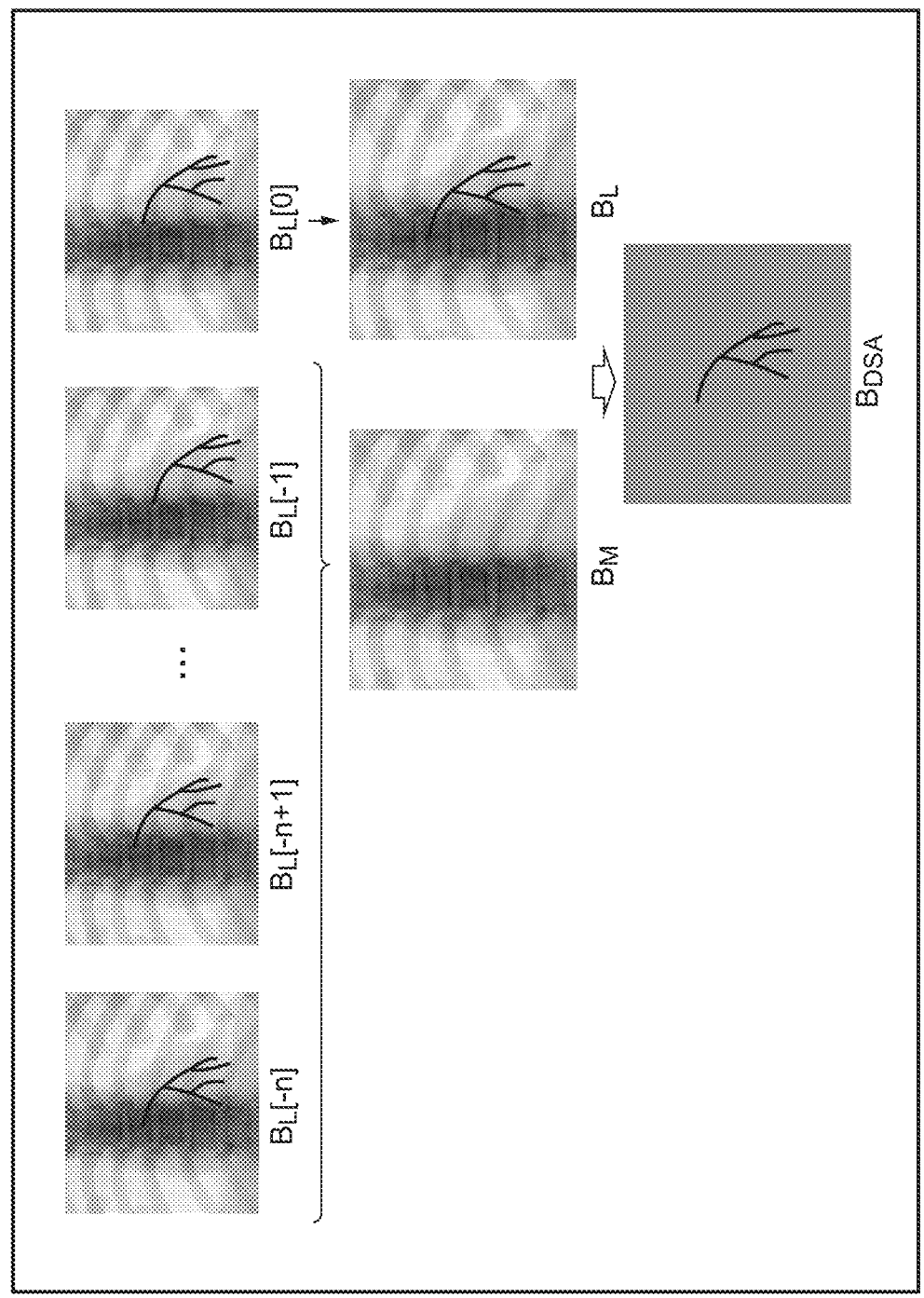
FIG. 11 is a schematic diagram illustrating processing that uses digital subtraction angiography according to the second embodiment.

FIG. 11 is a schematic diagram of image processing according to the third embodiment. For ease of description, a case is envisioned in which a live image is imaged while injecting a contrast agent into a coronary artery of a heart. The live image $H_L$ at high energy and the live image $L_L$ at low energy include information regarding bones, soft tissue, and the contrast agent. If energy subtraction is performed on these live images, information regarding the contrast agent that is a third substance appears in the live image $B_L$ of the bones. Accordingly, the live image $B_L$ of the bones may include information regarding the bones and the contrast agent.

At this time, blood vessels move as the heart beats, and thus the contrast agent also moves along with the blood vessels. On the other hand, the bones do not move as the heart beats. Accordingly, if a focus is placed on a time series of a certain pixel in the live image $B_L$ of the bones, there are a frame that includes only information regarding a bone and a frame that includes information regarding the bone and the contrast agent. Specifically, when a blood vessel into which the contrast agent was injected enters the region of the pixel, the pixel value of the live image $B_L$ of the bone increases in an amount of the contrast agent. Therefore, when the smallest value is taken for each pixel in the n images from the live image $B_L[-n]$ of the bones of the n-th frame before the current frame to the live image $B_L[-1]$ of the bones of the first frame before the current frame, information regarding the moving contrast agent is removed, and only information regarding the bones that do not move remains, if this (the mask image $B_M$ of the bones is subtracted from the live image $B_L$ of the bones of the current frame, a DSA image $B_{DSA}$ of the bones is obtained. In the DSA image $B_{DSA}$ of the bones, information regarding the bone is offset, and only information regarding the contrast agent remains. In this manner, even if movement occurs due to heartbeats, it is possible to image only the contrast agent, and to diagnose the blood vessels.

Note that, in the description of the third embodiment given with reference to FIG. 11, a case is envisioned in which a live image is imaged while a contrast agent is injected into a coronary artery of a heart, but this embodiment is not limited to such a case. For example, a case is conceivable in which imaging is performed while a guide wire, a stent, or the like is inserted into a coronary artery of a heart. At this time, similarly to the case of a contrast agent, blood vessels move as the heart beats, and thus, the guide wire or stent inserted through the blood vessel also moves. Therefore, when energy subtraction is performed on a live image obtained through imaging, information regarding the guide wire or stent (iron) that is a third substance appears in the live image $B_L$ of the bones. Also in this case, similar to the description given with reference to FIG. 11, when the blood vessel into which the guide wire or stent is inserted enters the region of a certain pixel, the pixel value of the live image $B_L$ of the bones increase in an amount of the guide wire or stent. Therefore, in the n images from the live image $B_L[-n]$ of the bones of the n-th frame before the current frame to the live image $B_L[-1]$ of the bones of the first frame before the current frame, when the smallest value is taken for each pixel, information regarding the guide wire or stent that moves is removed, and only information regarding the bones that do not move remains. Thus, in the DSA image $B_{DSA}$ of the bones, the information regarding the bones is offset, and only the information regarding the guide wire or stent remains. Accordingly, the guide wire or stent can be selectively imaged. A mode for selectively imaging a stent when intravascular surgery is complete and the stent is placed in a coronary artery and a mode for selectively imaging calcification (calcium) that is deposited in a coronary artery of a heart, as a result of performing similar processing, are suitably used. In addition, in the third embodiment, an example has been illustrated in which coronary arteries of a heart are imaged, but there is no limitation to such a mode. For example, there is the issue that, during contrast imaging of an abdominal aorta, a kidney or the like, an artifact is created in a DSA image due to vertical movement of a thoracic diaphragm accompanying breathing, bowel peristalsis, or the like. If this embodiment is applied to such a situation, it is possible to selectively image a contrast agent, a stent, and calcification even if a thoracic diaphragm or bowel moves.

In FIG. 11 of the third embodiment, the mask image $B_M$ of the bones is generated by taking the smallest value for each pixel in n images (n≥2) from the live image $B_L[-n]$ of the bones of the n-th frame before the current frame to the live image $B_L[-1]$ of the bones of the first frame before the current frame, in other words, an image of a plurality of past frames. However, this embodiment is not limited to such a mode. For example, when there is a live image $B_L$ of bones of a plurality of past frames, a mask image $B_M$ of the bones may be generated by calculating a statistic amount such as a maximum value, an average value, or a median value for each pixel. In addition, the mask image $B_M$ of bones may also be generated by removing an abnormal value for each pixel. For example, in a live image $B_L$ of bones, there is substantially no movement in the image of the bone, but a blood vessel through which a contrast agent passes moves, and thus the image of the bones can be remained by determining a change in each pixel value caused by the contrast agent as an abnormal value. Furthermore, a mask image $B_M$ of bones may also be generated by applying a recursive filter to a live image $B_L$ of the bones. As described above, a mask image $B_M$ of bones may be generated from a live image $B_L$ of the bones of a plurality of past frames using any method.

Moreover, the live image $B_L$ of bones has been described above, but this embodiment is not limited to such a mode. The mask image SM of soft tissue may also be generated from the live image SL of the soft tissue of a plurality of past frames.

In addition, as in the second embodiment, also when a live image $H_L$ at high energy and a live image $L_L$ at low energy are separated into an image of an effective atomic number Z and an image of an area density D, the above-described processing according to the third embodiment can be applied. In this case, a mask image $Z_M$ of the effective atomic number may be generated from a live image $Z_L$ of the effective atomic number of a plurality of past frames, and a mask image $D_M$ of the area density may be generated from a live image $D_L$ of the area density of a plurality of past frames.

As described above, according to the third embodiment, an image obtained from a plurality of radiation images at different energies through energy subtraction is used as a live image after energy subtraction. A mask image after energy subtraction is then generated from the live image of a plurality of past frames after energy subtraction. Subsequently, a DSA image after energy subtraction is generated by subtracting the mask image after energy subtraction generated as described above from the live image of the current frame after energy subtraction. Therefore, for example, even if the mask image includes a moving object other than soft tissue, such as a stent or calcification, it is possible to reduce creation of an artifact in a DSA image.

Fourth Embodiment

Next, a fourth embodiment will be described. According to the first embodiment, Expression 4 in the signal processing shown in FIG. 6A is solved though approximation of monochromatic radiation. However, usually, when radiation passes through a substance, a phenomenon called beam hardening occurs in which lower energy is absorbed more, and, as a result, the energy peak shifts higher. Therefore, when the thickness of a subject increases, the average energy of radiation shifts on a higher-energy side due to this beam hardening. Accordingly, there is the possibility that there will be a difference between the bone thickness B and the soft tissue thickness S. In view of this, according to the fourth embodiment, changes in the attenuation rate caused by changes in the thickness of the bone that is a first substance and in the thickness of soft tissue that is a second substance is taken into consideration, and the thicknesses of the first substance and second substance are obtained from a high-energy image and a low-energy image. Specifically, as will be described below, the bone thickness B and the soft tissue thickness S are obtained by solving the non-linear simultaneous equation, namely Expression 4. The configuration and operations of the radiation imaging system 100 according to the fourth embodiment are similar to those in the first to third embodiments.

A case will be described in which the Newton-Raphson method is used as a representative method for solving a non-linear simultaneous equation. First, letting the number of iterations of the Newton-Raphson method be m, the thickness of a bone after m-th iteration be $B^m$, and the thickness of soft tissue after m-th iteration be $S^m$, an attenuation rate $H^m$ at high energy after m-th iteration and an attenuation rate $L^m$ at low energy after m-th iteration are expressed as the following expression.

$$L^m = \frac{\int_0^\infty N_L(E)\exp\{-\mu_B(E)B^m - \mu_S(E)S^m\}EdE}{\int_0^\infty N_L(E)EdE} \quad (19)$$

$$H^m = \frac{\int_0^\infty N_H(E)\exp\{-\mu_B(E)B^m - \mu_S(E)S^m\}EdE}{\int_0^\infty N_H(E)EdE}$$

In addition, a change rate of the attenuation rate when a thickness changes minutely is expressed as the following expression.

$$\frac{\partial H^m}{\partial B^m} = \frac{\int_0^\infty -\mu_B(E)N_H(E)\exp\{-\mu_B(E)B^m - \mu_S(E)S^m\}EdE}{\int_0^\infty N_H(E)EdE} \quad (20)$$

$$\frac{\partial L^m}{\partial B^m} = \frac{\int_0^\infty -\mu_B(E)N_L(E)\exp\{-\mu_B(E)B^m - \mu_S(E)S^m\}EdE}{\int_0^\infty N_L(E)EdE}$$

$$\frac{\partial H^m}{\partial S^m} = \frac{\int_0^\infty -\mu_S(E)N_H(E)\exp\{-\mu_B(E)B^m - \mu_S(E)S^m\}EdE}{\int_0^\infty N_H(E)EdE}$$

$$\frac{\partial L^m}{\partial S^m} = \frac{\int_0^\infty -\mu_S(E)N_L(E)\exp\{-\mu_B(E)B^m - \mu_S(E)S^m\}EdE}{\int_0^\infty N_L(E)EdE}$$

At this time, a bone thickness $B^{m+1}$ and a soft tissue thickness $S^{m+1}$ after the m+1st iteration are expressed as the following expression using an attenuation rate 14 at high energy and an attenuation rate L at low energy.

$$\begin{bmatrix} B^{m+1} \\ S^{m+1} \end{bmatrix} = \begin{bmatrix} B^m \\ S^m \end{bmatrix} + \begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} \begin{bmatrix} H - H^m \\ L - L^m \end{bmatrix} \quad (21)$$

Letting a determinant be det, an inverse matrix of a matrix of 2×2 is expressed as the following expression based on Cramer's rule.

$$\det = \frac{\partial H^m}{\partial B^m}\frac{\partial L^m}{\partial S^m} - \frac{\partial H^m}{\partial S^m}\frac{\partial L^m}{\partial B^m} \quad (22)$$

$$\begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} = \frac{1}{\det} \begin{bmatrix} \frac{\partial H^m}{\partial S^m} & -\frac{\partial H^m}{\partial S^m} \\ -\frac{\partial L^m}{\partial B^m} & \frac{\partial H^m}{\partial B^m} \end{bmatrix}^{-1}$$

Therefore, if Expression 22 is substituted in Expression 21, the following expression is obtained.

$$B^{m+1} = B^m + \frac{1}{\det}\frac{\partial L^m}{\partial S^m}(H - H^m) - \frac{1}{\det}\frac{\partial H^m}{\partial S^m}(L - L^m) \quad (23)$$

$$S^{m+1} = S^m + \frac{1}{\det}\frac{\partial L^m}{\partial B^m}(H - H^m) + \frac{1}{\det}\frac{\partial H^m}{\partial B^m}(L - L^m)$$

As a result of repeating such calculation, the difference between the attenuation rate $H^m$ at high energy after the m-th iteration and the attenuation rate at high energy obtained through actual measurement infinitely approximates to 0. The same applies to the attenuation rate L at low energy. Accordingly, the bone thickness $B^m$ after m-th iteration converges to the bone thickness B, and the soft tissue thickness $S^m$ after m-th iteration converges to the soft tissue thickness S. The non-linear simultaneous equation expressed as Expression 4 can be solved in this manner.

In addition, a similar solving method applies to calculation for obtaining the effective atomic number Z and the area density D such as those illustrated in the second embodiment. Accordingly, an image of the effective atomic number and an image of the area density can be obtained based on a high-energy image and a low-energy image in consideration of a change in the attenuation rate caused by a change in the effective atomic number and a change in the area density. For example, a case will be described in which a non-linear simultaneous equation, namely Expression 10 is solved using the Newton-Raphson method. First, letting the number of iterations of the Newton-Raphson method be m, an effective atomic number after m-th iteration be $Z^m$, and an area density after m-th iteration be $D^m$, the attenuation rate $H^m$ at high energy after the m-th iteration and the low-energy attenuation rate $L^m$ after the m-th iteration are expressed as the following expression.

$$L^m = \frac{\int_0^\infty N_L(E)\exp\{-\mu(Z^m, E)D^m\}EdE}{\int_0^\infty N_L(E)EdE} \quad (24)$$

-continued $$H^m = \frac{\int_0^\infty N_H(E)\exp\{-\mu(Z^m, E)D^m\}EdE}{\int_0^\infty N_H(E)EdE}$$

In addition, the change rate of the attenuation rate when the effective atomic number and the area density minutely change is expressed as the following expression.

$$\frac{\partial H^m}{\partial Z^m} = \frac{\int_0^\infty -\frac{\partial \mu(Z^m, E)}{\partial Z^m}D^m N_H(E)\exp\{-\mu(Z^m, E)D^m\}EdE}{\int_0^\infty N_H(E)EdE} \quad (25)$$

$$\frac{\partial L^m}{\partial Z^m} = \frac{\int_0^\infty -\frac{\partial \mu(Z^m, E)}{\partial Z^m}D^m N_L(E)\exp\{-\mu(Z^m, E)D^m\}EdE}{\int_0^\infty N_L(E)EdE}$$

$$\frac{\partial H^m}{\partial D^m} = \frac{\int_0^\infty -\mu(Z^m, E)N_H(E)\exp\{-\mu(Z^m, E)D^m\}EdE}{\int_0^\infty N_H(E)EdE}$$

$$\frac{\partial L^m}{\partial D^m} = \frac{\int_0^\infty -\mu(Z^m, E)N_L(E)\exp\{-\mu(Z^m, E)D^m\}EdE}{\int_0^\infty N_L(E)EdE}$$

At this time, the bone thickness $B^{m+1}$ and the soft tissue thickness $S^{m+1}$ after the m+1st iteration are expressed as the following expression using the attenuation rate H at high energy and the attenuation rate L at low energy.

$$\begin{bmatrix} Z^{m+1} \\ D^{m+1} \end{bmatrix} = \begin{bmatrix} Z^m \\ D^m \end{bmatrix} + \begin{bmatrix} \frac{\partial H^m}{\partial Z^m} & \frac{\partial H^m}{\partial D^m} \\ \frac{\partial L^m}{\partial Z^m} & \frac{\partial L^m}{\partial D^m} \end{bmatrix}^{-1} \begin{bmatrix} H - H^m \\ L - L^m \end{bmatrix} \quad (26)$$

Letting a determinant be det, an inverse matrix of a matrix of 2×2 is expressed as the following expression based on Cramer's rule.

$$\det = \frac{\partial H^m}{\partial Z^m}\frac{\partial L^m}{\partial D^m} - \frac{\partial H^m}{\partial D^m}\frac{\partial L^m}{\partial Z^m} \quad (27)$$

$$\begin{bmatrix} \frac{\partial H^m}{\partial Z^m} & \frac{\partial H^m}{\partial D^m} \\ \frac{\partial L^m}{\partial Z^m} & \frac{\partial L^m}{\partial D^m} \end{bmatrix}^{-1} = \frac{1}{\det} \begin{bmatrix} \frac{\partial L^m}{\partial D^m} & -\frac{\partial H^m}{\partial D^m} \\ -\frac{\partial L^m}{\partial Z^m} & \frac{\partial H^m}{\partial Z^m} \end{bmatrix}^{-1}$$

Therefore, if Expression 27 is substituted in Expression 26, the following expression is obtained.

$$Z^{m+1} = Z^m + \frac{1}{\det}\frac{\partial L^m}{\partial D^m}(H - H^m) - \frac{1}{\det}\frac{\partial H^m}{\partial D^m}(L - L^m) \quad (28)$$

$$D^{m+1} = D^m - \frac{1}{\det}\frac{\partial L^m}{\partial Z^m}(H - H^m) + \frac{1}{\det}\frac{\partial H^m}{\partial Z^m}(L - L^m)$$

As a result of repeating such calculation, the difference between the attenuation rate $H^m$ at high energy after the m-th iteration and the attenuation rate H at high energy obtained through actual measurement infinitely approximates to 0. The same applies to the attenuation rate L at low energy. Accordingly, the effective atomic number $Z^m$ after the m-th iteration converges to the effective atomic number Z, and the area density $D^m$ after the m-th iteration converges to the area density D. In this manner, the non-linear simultaneous equation expressed as Expression 10 can be solved.

Note that solving a non-linear simultaneous equation using the Newton-Raphson method has been described in the fourth embodiment, but there is no limitation to such a mode. Iterative solution techniques such as the least-squares method and bisection method may also be used. In addition, when using an iterative solution technique, a bone thickness $B^0$ and a soft tissue thickness $S^0$ when no iteration has been performed, in other words initial values of the thickness of a bone and the thickness of soft tissue are necessary. Any constants can be provided as the initial values. In addition, as described in the first embodiment, a configuration is suitably used in which the thickness of a bone and the thickness of soft tissue are obtained using Expression 8 for approximation of the spectrum of radiation using monochromatic radiation, and are used as initial values. Similarly, in the case of the effective atomic number Z and the area density D described in the second embodiment, a configuration is suitably used in which the effective atomic number and the area density are obtained using Expression 14 in which the spectrum of radiation is approximated as monochromatic radiation, and these are used as initial values. The bone thickness B, the soft tissue thickness S, the effective atomic number Z and the area density D can be accurately obtained by performing the above-described calculation.

In addition, in the above description, the non-linear simultaneous equations expressed as Expressions 4 and 10 are solved using the iterative solution technique. However, in this process, when performing calculation of Expressions 19, 20, 24, and 25, numerical integral is necessary. Moreover, every time in iterative calculations are performed, calculation needs to be performed again. Furthermore, such computation needs to be performed for all of the pixels. Therefore, there is the issue that signal processing of energy subtraction shown in FIGS. 6A and 6B takes time. Particularly in this embodiment, moving image radiographing is envisioned, and thus a time allowed for signal processing is one or less frames. For example, if the frame rate is 20 fps, and if signal processing and image processing are not performed at 50 ms or lower, the processing does not catch up. In view of this, a configuration may also be adopted in which bone thicknesses B and soft tissue thicknesses S for various combinations of the attenuation rate H at high energy and the attenuation rate L at low energy are obtained in advance, to generate a table, and the bone thickness B and the soft tissue thickness S are obtained at a high speed by referencing this table.

Figure 12:
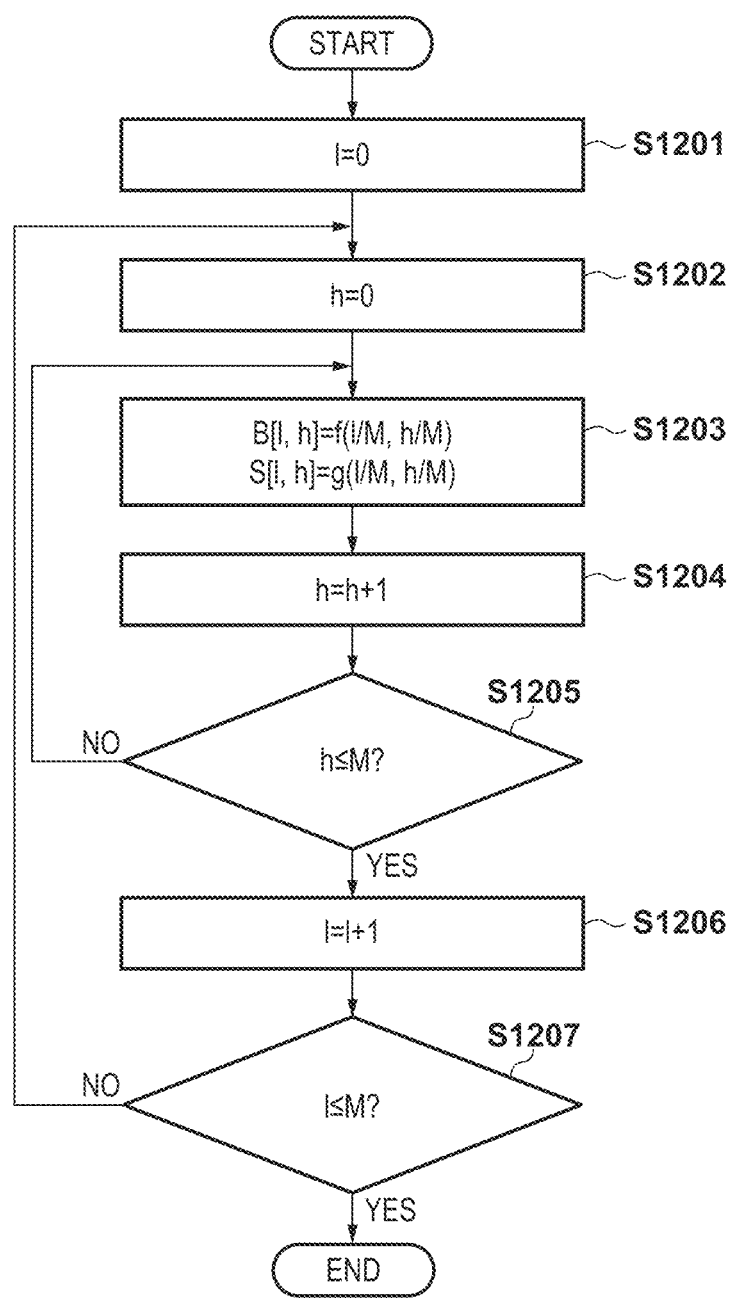
FIG. 12 is a flowchart showing table generation processing according to a fourth embodiment.

FIG. 12 shows a flowchart of table generation according to the fourth embodiment. A number of division of a table is indicated by M, a coordinate of low energy of the table is indicated by l, and a coordinate of high energy of the table is indicated by H. Note that the coordinates l and h of the table are integers. First, the control computer 103 initializes the coordinate of low energy as l=0 (step S1201), and the initializes the coordinate of high energy as h=0 (step S1204).

Next, the control computer 103 obtains an attenuation rate L[l] at low energy at the coordinate l and an attenuation rate H[h] at high energy at the coordinate h using the following expression.

$$H[h]=h/M$$

$$L[l]=l/M \tag{29}$$

The non-linear simultaneous equation expressed as Expression 4 is solved for the attenuation rate L[l] at low energy and the attenuation rate H[h] at high energy obtained in this manner, and the bone thickness B and the soft tissue thickness S are obtained. The result of this is stored in a table B[l,h] for the bone thickness B and a table S[l,h] for the soft tissue thickness S (step S1203). Subsequently, the control computer 103 performs settings of h=h+1 (step S1204). If the coordinate h for high energy does not exceed the number of division M of the table (NO in step S1205), the control computer 103 repeats the processing of step S1203 onward. If the coordinate h for high energy exceeds the number of division M of the table (YES in step S1205), the control computer 103 performs settings of l=l+1 (step S1206). Then, if the coordinate l for low energy does not exceed the number of division M of the table (NO in step S1207), the control computer 103 performs settings of h=0 (step S1202), and repeats the processes of steps S1203 to S1205. If the coordinate l for low energy exceeds the number of division M of the table (YES in step S1207), table generation ends. In this manner, bone thicknesses B and soft tissue thicknesses S can be obtained for all of the combinations of l and h, and can be stored in a table.

Figure 13:
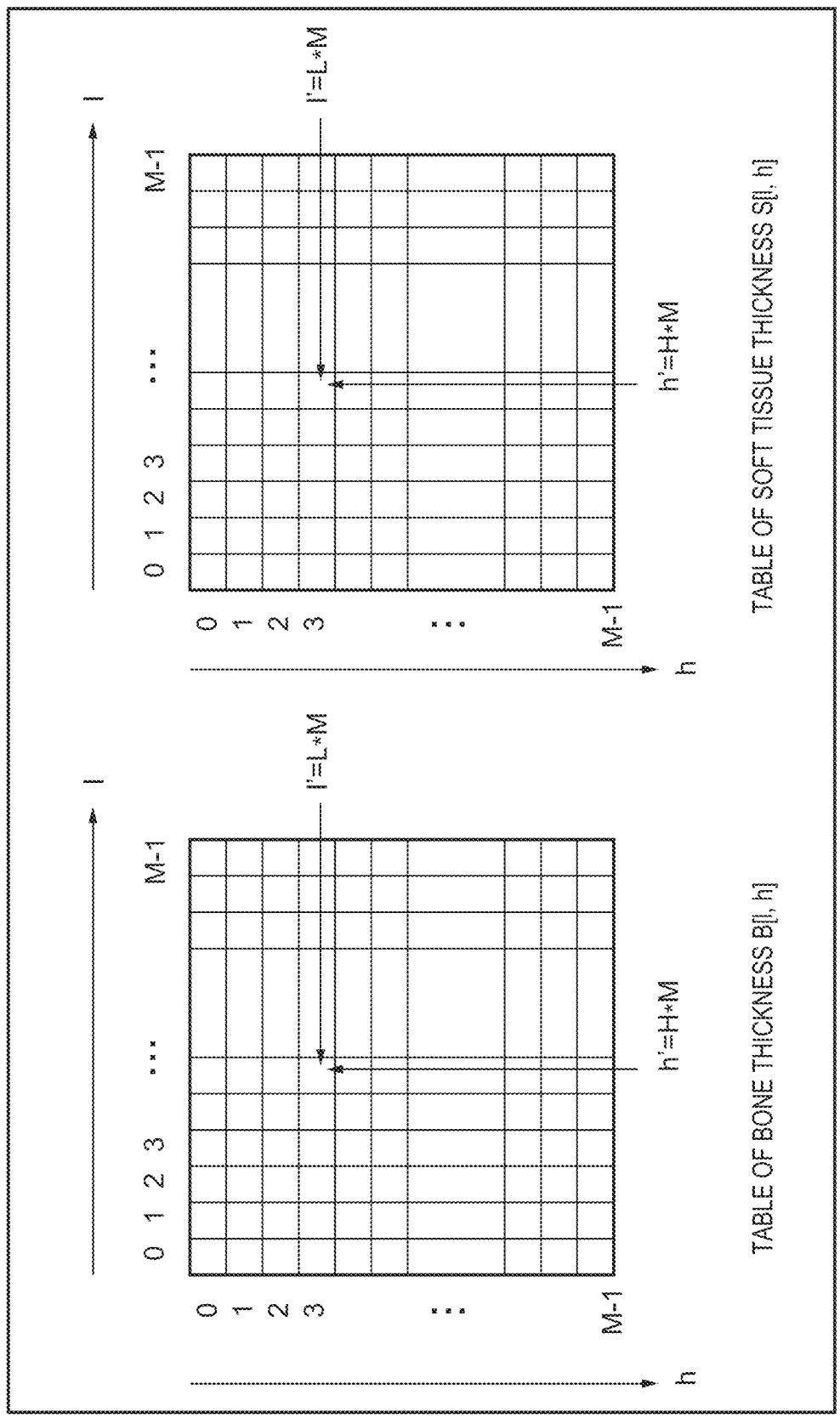
FIG. 13 is a schematic diagram showing table referencing according to the fourth embodiment.

FIG. 13 is a schematic diagram of table referencing according to the fourth embodiment. This table is a two-dimensional table in which a thickness of a bone and a thickness of soft tissue are registered for each combination of an attenuation rate indicated by a high-energy image and an attenuation rate indicated by a low-energy image. Assume that, at a certain pixel, an attenuation rate at low energy is denoted by L, and an attenuation rate at high energy is denoted by H. At this time, the attenuation rates are converted into the coordinates l' and h' of the table using the following expression.

$$h+=H*M$$

$$l'=L*M \tag{30}$$

The bone thickness B can be obtained by referencing the table B[l,h] for the bone thickness B using the coordinates. The same applies to the thickness of soft tissue. However, the coordinates l' and h' of the table have digits after the decimal point, but table is stored in an array, and thus the table can be referenced. only by using integers. Therefore, a configuration is suitably used in which the coordinates l' and h' are converted into integers, and the bone thickness B and the soft tissue thickness S are then obtained through interpolation. For example, letting a value obtained by rounding down/converting the coordinate l' to/into an integer be 1, and a value obtained by rounding down/converting the coordinate h' to/into an integer be h, if the bone thickness B and the soft tissue thickness S are obtained through bi-linear interpolation, the following expression is used.

$$B=\{B[l,h](h+1-W)+B[l,h+1](h'-h)\}(l+1-l')+ \\ \{B[l+1,h](h+1-h')+B[l+1,h+1](h'-h)\}(l'-l)$$

$$S=\{S[l,h](h+1-h')+S[l,h+1](h'-h)\}(l+1-l')+\{S[l+1,h] \\ (h+1-h')+S[l+1,h+1](h'-h)\}(l'-l) \tag{31}$$

Therefore, if a table is generated in advance, the bone thickness B and the soft tissue thickness S can be obtained with a dramatically smaller calculation amount than the calculation amount for solving a non-linear simultaneous equation. Such a table is effective unless the spectrum of radiation N(E) changes. In general, the spectrum of radiation N(E) does not change during moving image radiographing, and thus it is sufficient that a table is generated once before imaging. As a matter of course, generation and referencing of a table shown in FIGS. 12 and 13 can be used also in calculation for obtaining the thicknesses of any two substances similarly. The generation and referencing of a table shown in FIGS. 12 and 13 can also be used similarly in calculation for obtaining the effective atomic number Z and the area density D. In this case, a two-dimensional table in which an effective atomic number and an area density are registered for each combination of an attenuation rate indicated by a high-energy image and an attenuation rate indicated by a low-energy image is used. In this manner, signal processing of energy subtraction shown in FIGS. 6A and 6B can be accurately performed at a high speed.

Note that, according to the fourth embodiment, the attenuation rate L[l] at low energy at the coordinate l and the attenuation rate H[h] at high energy at the coordinate h are obtained using Expression 29. In a table generated in this manner, the coordinate of the vertical axis indicates the attenuation rate H at high energy, and the coordinate of the horizontal axis indicates the attenuation rate L at low energy, but attenuation rates from 0 to 1 in the table are divided equally. However, in most cases, an attenuation rate for the composition and thickness of a human body takes a value that is in the vicinity of 0. Therefore, there is a disadvantage that, if the number of division M of the table is small, the difference between a value obtained through referencing and interpolation of the table and a value obtained by solving the non-linear simultaneous equation is large. In view of this, a configuration is suitably used in which, letting a constant for determining the range of a coordinate be k (0<k), an attenuation rate is obtained using the following expression.

$$H[h] = \exp(-k*h/M)$$

$$L[l] = \exp(-k*l/M) \quad (32)$$

When an attenuation rate is obtained based on coordinates using Expression 32, the coordinates are obtained using the following expression.

$$h' = -\ln(H[h])*M/k$$

$$l' = -\ln(L[l])*M/k \quad (33)$$

Expression 31 is used for referencing and interpolation of the table. In the table generated in this manner, the coordinate of the vertical axis is −ln (H), and the coordinate of the horizontal axis is −ln (L). Therefore, even if the value of the attenuation rate is in the vicinity of 0, it is possible to decrease the difference between a value obtained by referencing and interpolation of the table and a value obtained by solving the non-linear simultaneous equation.

In addition, according to the fourth embodiment, when a table is generated and referenced, there may be a combination of the attenuation rate H at high energy and the attenuation rate L at low energy, for which there is no solution. For example, the attenuation rate H at high energy is usually larger than the attenuation rate L at low energy. Therefore, in the table generated using Expression 29 or 32, a solution for a region in which H<L is not obtained. In this embodiment, coordinates may be selected so as to reduce a region for which no solution is obtained from the table. The coordinate of the vertical axis may be ln(L)/ln(H), and the coordinate of the horizontal axis may be −ln(H), for example. Alternatively, as in Expressions 8 and 14, a value obtained through approximation as monochromatic radiation may also be used as the coordinate of the vertical axis, for example. In addition, when referencing the table in the fourth embodiment, there is the possibility that a coordinate outside of the range of the table will be specified, or a region for which a solution is not obtained will be referenced. In such a case, a configuration is suitably used in which the value of a region for which there is a solution is used, the region being near the specified coordinate.

Note that, according to the first embodiment, as shown in FIG. 7, image processing is performed in the order from performing energy subtraction and then performing DSA. However, when the spectrum of radiation N(E) is approximated using monochromatic radiation as in Expression 8, a configuration may also be adopted in which DSA is performed and energy subtraction is then performed. For example, if Expression 8 is applied to both a mask image and a live image, the bone thickness B and the soft tissue thickness S are expressed as the following expression.

$$\det = \mu_B(E_L)\mu_S(E_H) - \mu_B(E_H)\mu_S(E_L) \quad (34)$$

$$B_M \approx \frac{\mu_S(E_L)}{\det}\ln(H_M) - \frac{\mu_S(E_H)}{\det}\ln(L_M)$$

$$S_M \approx \frac{\mu_S(E_H)}{\det}\ln(L_M) - \frac{\mu_B(E_L)}{\det}\ln(H_M)$$

$$B_L \approx \frac{\mu_S(E_L)}{\det}\ln(H_L) - \frac{\mu_S(E_H)}{\det}\ln(L_L)$$

$$S_L \approx \frac{\mu_B(E_L)}{\det}\ln(L_L) - \frac{\mu_B(E_L)}{\det}\ln(H_L)$$

Based on Expression 34, DSA images are expressed as the following expressions.

$$\begin{aligned} B_{DSA} &= B_L - B_M \approx \frac{\mu_S(E_L)}{\det}\{\ln(H_L) - \ln(H_M)\} - \\ &\quad \frac{\mu_S(E_H)}{\det}\{\ln(L_L) - \ln(L_M)\} \\ &= \frac{\mu_S(E_L)}{\det}\ln\left(\frac{H_L}{H_M}\right) - \frac{\mu_S(E_H)}{\det}\ln\left(\frac{L_L}{L_M}\right) \end{aligned} \quad (35)$$

$$\begin{aligned} S_{DSA} &= S_L - S_M \approx \frac{\mu_B(E_H)}{\det}\{\ln(L_L) - \ln(L_M)\} - \\ &\quad \frac{\mu_H(E_L)}{\det}\{\ln(H_L) - \ln(H_M)\} \\ &= \frac{\mu_B(E_H)}{\det}\ln\left(\frac{L_L}{L_M}\right) - \frac{\mu_B(E_L)}{\det}\ln\left(\frac{H_L}{H_M}\right) \end{aligned}$$

Specifically, a result of subtracting a mask image from a live image and performing DSA after performing energy subtraction and a result of performing energy subtraction after dividing a live image by a mask image and performing DSA coincide. However, such randomness in the order of computation is not guaranteed in a configuration in which the non-linear simultaneous equation is solved for each pixel or a configuration in which the non-linear simultaneous equation is solved in advance and a table is generated and referenced, as in the fourth embodiment. Accordingly, there is the issue that, if DSA is performed and energy subtraction is then performed, the difference is large. On the other hand, if a configuration is adopted in which, after the non-linear equation is solved for each pixel and energy subtraction is performed, DSA is performed, the difference is small but there is the issue that the calculation amount is large. For such a reason, a table indicating the correspondence relation between pixel values for a plurality of different energies and pixel values after energy subtraction is desirably generated by solving the non-linear simultaneous equation, as illustrated in the fourth embodiment. The image processing unit 132 generates an image after energy subtraction by referencing the table generated in this manner, and the DSA processing unit 133 performs DSA using the image after energy subtraction.

Note that, according to the first to fourth embodiments, the radiation imaging apparatus 104 is an indirect-type radiation sensor that uses a fluorescent body, but there is no limitation to such a mode. For example, a direct-type radiation sensor that uses a direct conversion material such as CdTe may also be used. In addition, according to the first to fourth embodiments, for example, a passive change in the tube voltage of the radiation generation apparatus 101 is used, or the tube voltage is actively switched, but there is no limitation to such a mode. The energy of radiation that is irradiated to the radiation imaging apparatus 104 may be changed, for example, by switching the filter of the radiation generation apparatus 101 timewise.

Furthermore, according to the first to fourth embodiments, energy subtraction is performed by changing the energy of radiation that is irradiated to the radiation imaging apparatus 104, but there is no limitation to such a mode. For example, as described in the first embodiment, a scheme in which two sensors are stacked, and the spectra of radiation that are detected by the front-side sensor and the back-side sensor are different may also be used. In addition, a plurality of images at different energies may also be obtained by using a photon counting sensor that counts the number of radiation quanta for each energy.

In addition, according to the first and second embodiments, energy subtraction processing is performed using the control computer 103 of radiation imaging system, but there is no limitation to such a mode. A configuration may also be adopted in which an image obtained by the control computer 103 is transferred to another computer, which performs energy subtraction processing. For example, a configuration is suitably used in which an obtained image is transferred to another personal computer via a medical PACS, is subjected to energy subtraction processing, and is displayed. That is to say, in the above embodiments, it suffices for radiation images at different energies to be provided for energy subtraction processing, and a method for obtaining radiation images at different energies is not limited to the above embodiments.

According to the above embodiments, it is possible to further reduce creation of an artifact, in image generation that is based on a difference.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An imaging control apparatus comprising:
an obtaining unit configured to obtain a plurality of images at different radiation energies, the images having been obtained as a result of irradiating a subject with radiation whose energy changes during one shot, and detect, a plurality of times, the radiation that has passed through the subject during the one shot;
a first generation unit configured to generate an energy subtraction image by performing energy subtraction processing using a plurality of images; and
a second generation unit configured to generate a difference image using a plurality of energy subtraction images generated by the first generation unit.

2. The imaging control apparatus according to claim 1, wherein
the second generation unit generates a mask image using an energy subtraction image obtained by the first generation unit before a contrast agent is injected, generates a live image using an energy subtraction image obtained by the first generation unit after a contrast agent is injected, and generates a difference image between the mask image and the live image.

3. The imaging control apparatus according to claim 1, wherein
the second generation unit generates a mask image based on a processed image of a plurality of frames prior to a current frame included in an energy subtraction image obtained by the first generation unit, and generates, using an energy subtraction image of the current frame as a live image, a difference image between the mask image and the live image.

4. The imaging control apparatus according to claim 1, wherein
the first generation unit performs energy subtraction processing using a first image obtained at a first radiation energy and a second image obtained at a second radiation energy that is different from the first radiation energy, so as to generate a first energy subtraction image related to a thickness of a first substance, and a second energy subtraction image related to a thickness of a second substance that is different from the first substance, and
the second generation unit generates a difference image of digital subtraction angiography using the first energy subtraction image.

5. The imaging control apparatus according to claim 4, wherein
the first generation unit generates the first energy subtraction image and the second energy subtraction image based on linear attenuation coefficients of the first substance and the second substance at the first radiation energy, and linear attenuation coefficients of the first substance and the second substance at the second radiation energy.

6. The imaging control apparatus according to claim 4, wherein
the first substance is a bone, and the second substance is soft tissue.

7. The imaging control apparatus according to claim 4, wherein,
in consideration of a change in an attenuation rate caused by changes in a thickness of the first substance and a thickness of the second substance, the first generation unit obtains, from the first image and the second image, the first energy subtraction image related to the thickness of the first substance and the second energy subtraction image related to the thickness of the second substance.

8. The imaging control apparatus according to claim 7, wherein
the first generation unit references a two-dimensional table in which thicknesses of a first substance and a second substance are registered, in accordance with a combination of an attenuation rate indicated by the first image and an attenuation rate indicated by the second image.

9. The imaging control apparatus according to claim 1, wherein
the first generation unit performs energy subtraction processing using a first image obtained at a first radiation energy and a second image obtained at a second radiation energy that is different from the first radiation energy, and obtains an image of an effective atomic number and an image of an area density as the energy subtraction images.

10. The imaging control apparatus according to claim 9, wherein
the second generation unit generates a difference image of digital subtraction angiography, using images of the effective atomic number obtained by the first generation unit before and after a contrast agent is injected.

11. The imaging control apparatus according to claim 9, wherein
the second generation unit generates a difference image of digital subtraction angiography, using images of the effective atomic number and the area density obtained by the first generation unit before and after a contrast agent is injected.

12. The imaging control apparatus according to claim 11, wherein
letting mask images generated based on the image of the effective atomic number and the image of the area density be respectively $Z_M$ and $D_M$, and live images generated based on the image of the effective atomic number and the image of the area density be respectively $Z_L$ and $D_L$, the second generation unit generates a difference image $D_{DSA}$ of an area density and a difference image $Z_{DSA}$ of an effective atomic number using:

$$D_{DSA} = D_L - D_M$$

-continued $$Z_{DSA} = \sqrt[n]{Z_L^n * \frac{D_L}{D_{DSA}} - Z_M^n * \frac{D_M}{D_{DSA}}}$$

(wherein n is a real number larger than or equal to 2.5 and smaller than or equal to 3).

13. The imaging control apparatus according to claim 11, wherein
the second generation unit generates a color image by determining hue H of an HLS color space based on a difference image of an effective atomic number, and determining lightness L of the HLS color space based on a difference image of an area density.

14. The imaging control apparatus according to claim 9, wherein
the first generation unit obtains an image of an effective atomic number and an image of an area density from the first image and the second image, in consideration of a change in an attenuation rate caused by a change in an effective atomic number and a change in area density.

15. The imaging control apparatus according to claim 14, wherein
the first generation unit references a two-dimensional table in which an effective atomic number and an area density are registered, in accordance with a combination of an attenuation rate indicated by the first image and an attenuation rate indicated by the second image.

16. The imaging control apparatus according to claim 1; wherein
the second generation unit generates the difference image for each imaging period of one frame.

17. An imaging control apparatus characterized by comprising:
an obtaining unit configured to obtain a first image and a second image at different radiation energies during an imaging period of one frame, as a result of a two-dimensional detector performing sampling at least twice during a period between two consecutive resets;
a first generation unit configured to generate an energy subtraction image by performing energy subtraction processing on the first image and the second image; and
a second generation unit configured to generate a difference image using a plurality of energy subtraction images.

18. An imaging control method for radiography, comprising:
obtaining a plurality of images at different radiation energies, the images having been obtained as a result of irradiating a subject with radiation whose energy changes during one shot, and detecting, a plurality of times, the radiation that has passed through the subject during the one shot;
generating an energy subtraction image by performing energy subtraction processing using a plurality of images; and
generating a difference image using a plurality of generated energy subtraction images.

19. An imaging control method for radiography, comprising:
obtaining a first image and a second image at different radiation energies during an imaging period of one frame, as a result of a two-dimensional detector performing sampling at least twice during a period between two consecutive resets;

generating an energy subtraction image by performing energy subtraction processing on the first image and the second image; and generating a difference image using a plurality of energy subtraction images.

20. A radiation imaging system comprising:

an imaging control apparatus comprising:

an obtaining unit configured to obtain a plurality of images at different radiation energies, the images having been obtained as a result of irradiating a subject with radiation whose energy changes during one shot, and detect, a plurality of times, the radiation that has passed through the subject during the one shot;

a first generation unit configured to generate an energy subtraction image by performing energy subtraction processing using a plurality of images; and a second generation unit configured to generate a difference image using a plurality of energy subtraction images generated by the first generation unit;

a radiation imaging apparatus that includes a two-dimensional detector; and a radiation generation apparatus that generates radiation.

21. A non-transitory computer-readable storage medium storing a program for causing a computer to execute an imaging control method for radiography, the method comprising:

obtaining a plurality of images at different radiation energies, the images having been obtained as a result of irradiating a subject with radiation whose energy changes during one shot, and detecting, a plurality of times, the radiation that has passed through the subject during the one shot;

generating an energy subtraction image by performing energy subtraction processing using a plurality of images; and generating a difference image using a plurality of generated energy subtraction images.

22. A non-transitory computer-readable storage medium storing a program for causing a computer to execute an imaging control method for radiography, the method comprising:

obtaining a first image and a second image at different radiation energies during an imaging period of one frame, as a result of a two-dimensional detector performing sampling at least twice during a period between two consecutive resets;

generating an energy subtraction image by performing energy subtraction processing on the first image and the second image; and generating a difference image using a plurality of energy subtraction images.

* * * * *